United States Patent [19]

Fujinami et al.

[11] 4,009,278
[45] Feb. 22, 1977

[54] ANTIMICROBIAL COMPOSITION AND METHOD CONTAINING N-(3,5-DIHALOPHENYL)-IMIDE COMPOUNDS

[75] Inventors: Akira Fujinami, Ashiya; Toshiaki Ozaki, Toyonaka; Shigehiro Ooba, Takarazuka; Sigeo Yamamoto, Toyonaka; Katsuji Nodera, Nishinomiya; Katsutoshi Tanaka, Takarazuka; Keiichiro Akiba, Ikeda; Tadashi Ooishi, Minoo; Nobuyuki Kameda, Takarazuka, all of Japan

[73] Assignee: Sumitomo Chemical Company, Limited, Osaka, Japan

[22] Filed: Apr. 24, 1975

[21] Appl. No.: 571,104

Related U.S. Application Data

[62] Division of Ser. No. 322,169, Jan. 9, 1973, Pat. No. 3,903,090, which is a division of Ser. No. 17,339, March 6, 1970, Pat. No. 3,745,170.

[30] Foreign Application Priority Data

Mar. 19, 1969 Japan .............................. 44-21529

[52] U.S. Cl. .................................. 424/274; 424/46; 424/357
[51] Int. Cl.² .......................................... A01N 9/22
[58] Field of Search ..................................... 424/274

[56] References Cited

UNITED STATES PATENTS 3,529,062  9/1970  Renner .............................. 424/274
3,530,126  9/1970  Bernasconi et al. ........... 424/274 X Primary Examiner—Dale R. Ore
Attorney, Agent, or Firm—Stevens, Davis, Miller & Mosher

[57] ABSTRACT

Novel N-(3,5-dihalophenyl)imide compounds, which exhibit a strong antimicrobial activity against microorganisms including phytopathogenic fungi, parasites of industrial products and pathogenic microorganisms, represented by the formula,

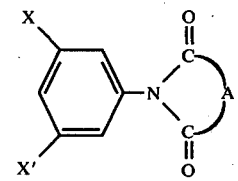

wherein X and X' each represent halogens and A represents a substituted ethylene such as chloroethylene, $C_1 - C_4$ alkylthioethylene, $C_1 - C_2$ alkyl-ethylene or 1,2-di-$C_1 - C_2$-alkyl-ethylene, a cyclopropylene such as 1,3-dimethylcyclopropylene, trimethylene, a cyclohexylene-1,2-, cyclohexenylene-1,2-, cyclohexadienylene-1,2- or o-phenylene.

The N-(3,5-dihalophenyl)imide compounds can be obtained by any of methods which produce imide compounds or reaction of an N-(3,5-dihalophenyl)maleimide compound with a mercaptan, a hydrogen halide, phosphorus chloride or thionylchloride.

9 Claims, No Drawings

ANTIMICROBIAL COMPOSITION AND METHOD CONTAINING N-(3,5-DIHALOPHENYL)-IMIDE COMPOUNDS

This is a Division of application Ser. No. 322,169, filed Jan. 9, 1973, now U.S. Pat. No. 3,903,090, which is a Division of application Ser. No. 17,339, filed Mar. 6, 1970, now U.S. Pat. No. 3,745,170.

The present invention relates to novel N-(3,5-dihalophenyl)imide compounds and their production and use.

The said N-(3,5-dihalopenyl)imide compounds are represented by the formula,

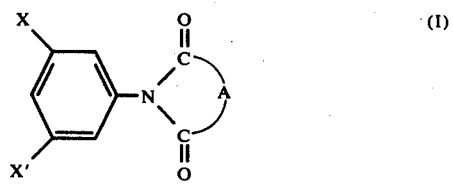

wherein X and X' represent halogen atoms, and A represents a substituted ethylene group of the formula,

wherein $R_1$ is alkyl of 1–4 carbon atoms, halogen, alkylthio of 1–10 carbon atoms, lower alkenylthio, lower acylthio, aralkylthio, phenylthio, halogenated phenylthio, methylated phenylthio, nitrated phenylthio, dialkylamino (the alkyl group has 1–6 carbon atoms), cyclic secondary amino of 4–5 carbon atoms, morpholino, alkylsulfinyl of 1–10 carbon atoms or aralkylsulfinyl, and $R_2$ is hydrogen, alkyl of 1–4 carbon atoms or halogen, provided that $R_1$ is alkyl if $R_2$ is alkyl, $R_1$ is halogen if $R_2$ is halogen, and $R_1$ is other than alkyl if $R_2$ is hydrogen, or A represents a cyclopropylene group represented by the formula,

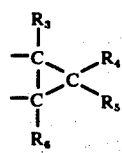

wherein $R_3$, $R_4$, $R_5$ and $R_6$ each represents hydrogen or alkyl of 1–4 carbon atoms, or A represents trimethylene, cyclohexylene-1,2-, cyclohexenylene-1,2-, cyclohexadienylene-1,2- or o-phenylene.

In the present invention, examples of the halogen atom include chlorine, bromine, iodine and fluorine, and examples of the cyclic secondary amino group include pyrrolidino and piperidino.

It has now been found that the said N-(3,5-dihalophenyl)imide compounds of the formula (I) exhibit a strong anti-microbial activity against a wide variety of microorganisms including phytopathogenic fungi and parasites of industrial products, and some of them further possess strong anti-microbial activity against pathogenic microorganisms. This finding is unexpectable and surprising because compounds analogous thereto such as the corresponding 3,5-unhalogenated derivative show no appreciable anti-microbial activity. In this connection, it may be noted that some of such analogous compounds exert a strong herbicidal activity, whereas the compounds of the present invention have no herbicidal action.

A fundamental object of the present invention is to provide the novel N-(3,5-dihalophenyl)imide compounds (I) having a marked anti-microbial activity.

Another object of the invention is to provide a process for preparing the N-(3,5-dihalophenyl)imide compounds (I).

Other objects will become apparent from the following description.

In accordance with the present invention, the N-(3,5-dihalophenyl)imide compounds (I) are prepared according to any of the procedures represented by the equations shown below.

PROCEDURE 1

In the case where, in the aforesaid formula (I), A is other than an alkylsulfinyl ethylene or aralkylsulfinyl ethylene group, i.e. $R_1$ is other than an alkylsulfinyl or aralkylsulfinyl group:

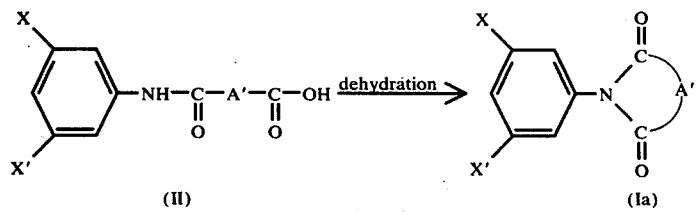

PROCEDURE 2

In the case where, in the formula (I), A is a substituted ethylene group, in which $R_2$ is hydrogen and $R_1$ is alkylthio, lower alkenylthio, lower acylthio, aralkylethio, halogenated phenylthio, methylated phenylthio, nitrated phenylthio, dialkylamino, cyclic secondary amino, morpholino or halogen:

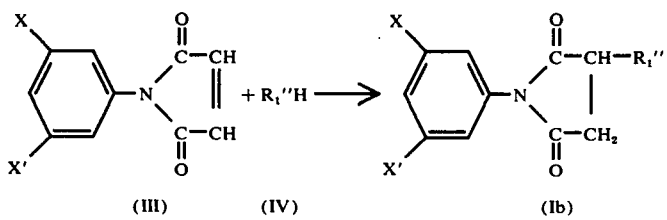

PROCEDURE 3

In the case where, in the formula (I), A is a substituted ethylene group, in which $R_2$ is hydrogen and $R_1$ is chlorine:

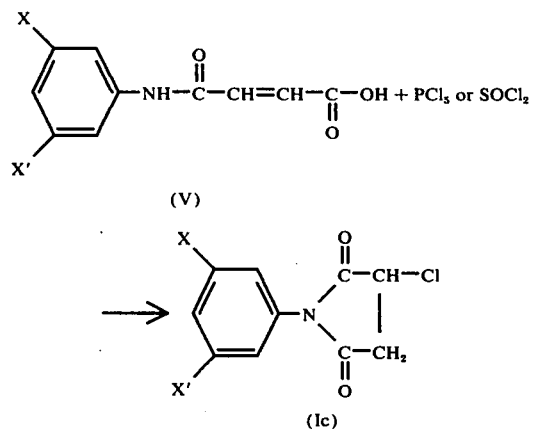

PROCEDURE 4

In the case where, in the formula (I), A is a substituted ethylene group, in which $R_2$ is hydrogen and $R_1$ is alkylsulfinyl or aralkylsulfinyl:

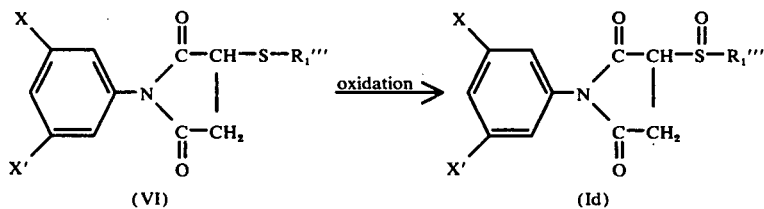

In the above-mentioned formulas of the procedures 1–4, X and X' are as defined previously, A' is a substituted ethylene group represented by the formula,

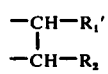

wherein $R_2$ is as defined previously, and $R_1'$ is alkyl of 1–4 carbon atoms, halogen, alkylthio of 1–10 carbon atoms, lower alkenylthio, lower acylthio, aralkylthio, phenylthio, halogenated phenylthio, methylated phenylthio, nitrated phenylthio, dialkylamino (the alkyl group has 1–6 carbon atoms), cyclic secondary amino of 4–5 carbon atoms or morpholino, provided that $R_1'$ is alkyl if $R_2$ is alkyl, $R_1'$ is halogen if $R_2$ is halogen and $R_1'$ is other than alkyl if $R_2$ is hydrogen, or a cyclopropylene group represented by the formula,

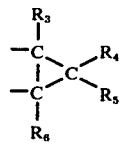

wherein $R_3$, $R_4$, $R_5$ and $R_6$ are as defined previously, or trimethylene, cyclohexylene-1,2-, cyclohexenylene-1,2-, cyclohexadienylene-1,2- or o-phenylene; $R_1''$ is alkylthio of 1–10 carbon atoms, lower alkenylthio, lower acylthio, aralkylthio, phenylthio, halogenated phenylthio, dialkylamino (the alkyl group has 1–6 carbon atoms), cyclic secondary amino of 4–5 carbon atoms, morpholino or halogen; $R_1'''$ is alkyl of 1–10 carbon atoms, aralkyl or lower alkenyl.

On the basis of each of the above-mentioned procedures, the process of the present invention is explained below.

PROCEDURE 1

This procedure is due to the dehydration reaction of a mono-N-(3,5-dihalophenyl)amide of dicarboxylic acid compound (II). According to this procedure, all the N-(3,5-dihalophenyl)imide compounds of the present invention can be synthesized, except the case where A in the formula (I) is alkylsulfinyl ethylene or aralkylsulfinyl ethylene. When this procedure is adopted, the desired N-(3,5-dihalophenyl)imide compounds (Ia) can be easily prepared by merely heating the mono-N-(3,5-dihalophenyl)amide of dicarboxylic acid compound (II) to 150° – 250° C., preferably 180° – 200° C., or by bringing the said compound (II) into contact with a suitable dehydrating agent at 20° – 150° C., preferably 60° – 100° C. Examples of the dehydrating agent include acid anhydrides such as acetic anhydride, phosphorus pentachloride, phosphorus oxychloride, phosphorus pentoxide, acetyl chloride and thionyl chloride, but particularly preferable dehydrating agent is acetic anhydride. The amount of the dehydrating agent is more than an equimolar amount of the compound (II). The dehydration reaction proceeds even in the absence of a reaction medium, but is preferably effected in the presence of a heating medium or a solvent. Examples of the heating medium include xylene, liquid parafin, nitrobenzene, dichlorobenzene, etc., and examples of the solvent include benzene, toluene, xylene, chloroform, carbon tetrachloride, etc. The reaction terminates in a period of 30 minutes to 10 hours, in general.

In the case where, in the formula (II), X is identical with X' and the group A' is not symmetric, there are two kinds of plane structure isomers as the starting mono-N-(3,5-dihalophenyl)amide of dicarboxylic acid compound (II). No matter which starting material is used, however, the resulting N-(3,5-dihalophenyl)imide compound (Ia) is same in structure.

The mono-N-(3,5-dihalophenyl)amide of dicarboxylic acid compounds (II), which are used as the starting materials in this procedure, are novel compounds and are easily obtainable by reacting, for example, a corresponding 3,5dihaloaniline with a corresponding acid anhydride, as shown in the following equation:

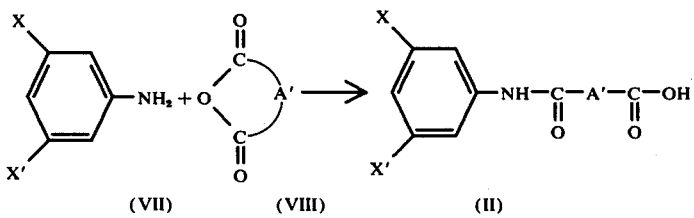

(VII)  (VIII)  (II)

PROCEDURE 2

This procedure is due to the addition reaction of N-(3,5-dihalophenyl)maleimide compounds (III) to carbon-carbon double bonds. The said addition reaction is accomplished by merely bringing the N-(3,5-dihalophenyl)maleimide compound (III) into contact with an equimolar amount or slight excess of a compound represented by the formula (IV). The reaction temperature varies depending on the kind of $R_1''$, but, in general, is $-10°$ to $100°$ C., preferably $0°$ to $30°$ C., in case $R_1''$ is alkylthio, lower alkenylthio, lower acylthio, aralkylthio, phenylthio, halogenated phenylthio, methylated phenylthio, nitrated phenylthio, dialkylamino, cyclic secondary amino of 4–5 carbon atoms or morpholino, and is $0°$ to $100°$ C., preferably $20°$ to $50°$ C., in case $R_1''$ is halogen. The above-mentioned reaction is preferably effected in a solvent. The kind of the solvent used varies depending on the kind of $R_1''$. Generally, however, the solvent is selected from benzene, toluene, xylene, aliphatic hydrocarbon, solvents weak in polarity such as ether, chloroform, etc., dioxane, tetrahydrofuran, dimethylformamide, dimethylsulfoxide and the like. Further, in case $R_1''$ is other than halogen, a suitable basic catalyst is used. Whereby the reaction progresses easily. Examples of the basic catalyst include tertiary amines such as triethylamine, dimethylaniline, diethylaniline, pyridine, N-methylmorpholine and the like. Particularly, the use of triethylamine is preferable.

The N-(3,5-dihalophenyl)maleimide compounds (III), which are used as the starting materials in this procedure, are easily obtained by reacting, for example, a corresponding 3,5-dihaloaniline with maleic anhydride (refer to Dutch Patent Application No. 68-17250 filed by Sumitomo Chemical Co.) which corresponds to U.S. Pat. No. 3,586,697.

PROCEDURE 3

This procedure is due to the reaction of N-(3,5-dihalophenyl)maleamic acid compounds (V) with a chlorinating agent. The said reaction is effected by bringing the N-(3,5-dihalophenyl)maleamic acid compound into contact with an equimolar amount or slight excess of phosphorus pentachloride or thionyl chloride at $0°$ to $80°$ C., preferably $20°$ to $80°$ C. If necessary, the reaction is carried out in a suitable solvent. Examples of the solvent include chloroform, carbon tetrachloride, chlorobenzene, etc.

After completion of the reaction, the reaction product is washed with water, dried and then recrystallized from a suitable solvent such as, for example, benzene-ethanol, petroleum benzin-benzene, ligroin-benzene or n-hexane-benzene, whereby the desired product can be easily obtained.

The N-(3,5-dihalophenyl)maleamic acid compounds (V), which are used as the starting materials in this procedure, are readily obtainable by reacting, for example, a corresponding 3,5-dihaloaniline with maleic anhydride.

PROCEDURE 4

This procedure is due to the oxidation reaction of thioether compounds (VI). The oxidation reaction is easily accomplished by bringing the thioether compound (VI) into contact with at least a stoichiometric amount of a suitable oxidizing agent such as, for example, hydrogen peroxide, an organic peracid, i.e. performic, peracetic or perbenzoic acid, chromic acid or permanganate, at $0°$ to $40°$ C., preferably $20°$ to $30°$ C. In the case of employment of chromic acid or permanganate, it is desirable that the oxidizing agent is not used in large excess. The reaction is desirably effected in a solvent. Examples of the solvent include water and water-miscible solvents such as acetone, alcohol, acetic acid and the like. The thioether compounds (VI), which are used as the starting materials in this procedure, are obtained according to the aforesaid procedure 1 or 2.

The N-(3,5-dihalophenyl)imide compounds (I) obtained in the above manner are purified, if necessary, by a suitable means, e.g. by recrystallization from a proper solvent.

As mentioned previously, the N-(3,5-dihalophenyl)imide compounds (I) of the present invention exert a strong anti-microbial activity against various microorganisms including phytopathogenic fungi (e.g. *Pyricularia oryzae, Cochliobolus miyabeanus, Xanthomonas oryzae, Sphaerotheca fulginea, Pellicularia sasakii, Pellicularia filamentosa, Fusarium oxysporum, Corticium rolfsii, Botrytis cinerea, Sclerotinia sclerotiorum, Alternaria kikuchiana, Alternaria mali, Glomeralla cingulata* and *Pythium aphanidermatum*) and parasites of industrial products (e.g. *Aspergillus niger*) and pathogenic microorganisms (e.g. *Staphylococcus aureus, Escherichia coli, Trichophyton rubrum*).

Further, the characteristic physiological activity of the present compounds is observed only in the case where 3,5-dihalophenyl groups have been substituted in the nitrogen atoms of the imide compounds, and is not observed at all in the case where other phenyl groups have been substituted therein. In order to substantiate this and the fact that the present compounds have such strong and broad microbicidal effects as not seen in microbicides of the prior art, typical tests results are set forth below.

TEST 1

Each of the test compounds in the form of wettable powders was diluted with water to a given concentration and sprayed to rice plants, which had been cultured in pots of 9 cm. in diameter and grown up to the 3 leaves stage, in a proportion of 7 ml. of the dilution per pot. After 1 day, the plants were inoculated by spraying with a spore suspension of *Pyricularia oryzae*. 5 days thereafter, the number of diseased spots was counted. The results were as shown in the tables below, from which it is understood that the N-(3,5-dihalophenyl)imide compounds (I) are stronger in anti-fungal activity (against Rice blast) than compounds analogous thereto such as the corresponding other isomeric compounds.

Table 2

| No. | Compound | Concentration (p.p.m.) | No. of Diseased spots per 10 leaves |
|---|---|---|---|
| 1 | [structure: phthalimide N-(2,5-dichlorophenyl)] | 1,000 | 38 |

Table 1

| No. | Compound | Concentration (p.p.m.) | No. of Diseased spots per 10 leaves |
|---|---|---|---|
| 1 | [3,5-Cl₂-phenyl imide with –CH·SCH₂(CH₂)₂CH₃ and C–CH₂] | 1,000 | 28 |
| 2 | [3,5-Cl₂-phenyl imide with –CH–S–C₆H₅] | 1,000 | 0 |
| 3 | [3,5-Cl₂-phenyl imide with –CH–S–C₆H₄–Cl] | 1,000 | 8 |
| 4 | [3,5-Cl₂-phenyl imide with –CH–N-morpholino] | 1,000 | 36 |
| 5 | [3,5-Br₂-phenyl imide with –CH–S–C₆H₅] | 1,000 | 12 |
| 6 | Reference compound [phenyl imide with –CH–S–C₆H₅] | 1,000 | 256 |
| | Untreated | — | 286 |

Table 2-continued
| No. | Compound | Concentration (p.p.m.) | No. of Diseased spots per 10 leaves |
|---|---|---|---|
| 2 | 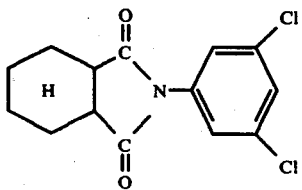 Reference compound | " | 56 |
| 3 | 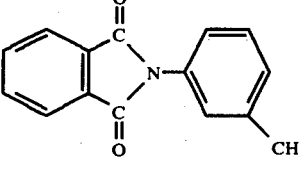 Reference compound | " | 312 |
| 4 | 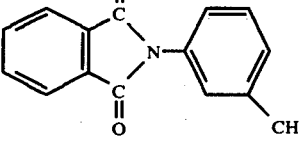 Reference compound | 1,000 | 264 |
| 5 | 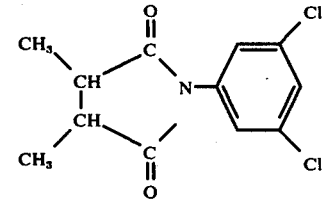 | " | 281 |
| Untreated | | — | 285 |
Table 3
| No. | Compound | Concentration (p.p.m.) | No. of Diseased spots per leaf |
|---|---|---|---|
| 1 | 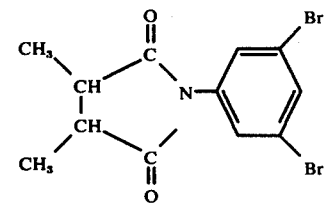 | 500 | 2.8 |
| 2 | 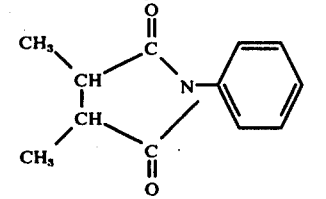 | 500 | 3.7 |
| 3 | 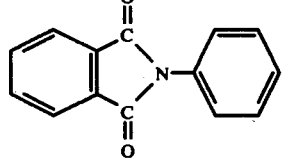 Reference compound | 500 | 36.7 |
| Untreated | | — | 38.9 |
Table 4
| No. | Compound | Concentration (p.p.m.) | No. of Diseased spots per leaf |
|---|---|---|---|
| 1 | 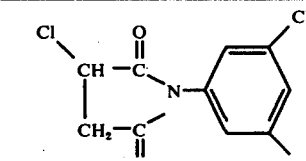 | 500 | 0.6 |
| 2 | 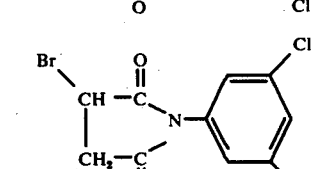 | 500 | 1.4 |

Table 4-continued

| No. | Compound | Concentration (p.p.m.) | No. of Diseased spots per leaf |
|---|---|---|---|
| 3 | Cl–CH–C(=O)–N(C₆H₃Br₂)–CH₂–C(=O) (3,5-dibromophenyl imide) | 500 | 1.2 |
| 4 | Reference compound: Cl–CH–C(=O)–N(C₆H₅)–CH₂–C(=O) | 500 | 33.8 |
| 5 | Reference compound: Cl–CH–C(=O)–N(C₆H₄NO₂)–CH₂–C(=O) (4-nitrophenyl) | 500 | 30.3 |

Table 4-continued

| No. | Compound | Concentration (p.p.m.) | No. of Diseased spots per leaf |
|---|---|---|---|
| 6 | Cl–CH–C(=O)–N(3-CH₃-C₆H₄)–CH₂–C(=O) | 500 | 35.1 |
| Untreated | | — | 34.5 |

Table 5

| No. | Compound | Concentration (p.p.m.) | No. of Diseased spots per leaf |
|---|---|---|---|
| 1 | 3,5-Cl₂-C₆H₃–N[C(=O)CH·SOCH₂CH₃][C(=O)CH₂] | 500 | 1.4 |
| Untreated | | — | 38.8 |

TEST 2

Each of the test compounds in the form of dusts was applied to rice plants, which had been cultured in pots of 9 cm. in diameter and grown up to the 4 leaves stage, in a proportion of 100 mg. of the dust per pot by use of a duster. After one day, the plants were inoculated by spraying with a spore suspension of *Cochliobolus miyabeanus*. 3 Days thereafter, the number of diseased spots was counted. The results were as shown in the tables below, from which it is understood that the N-(3,5-dihalophenyl)imide compounds (I) are stronger in anti-fungal activity (against Helminthosporium leaf spot of rice) than compounds analogous thereto such as the corresponding other isomeric compounds.

Table 6

| No. | Compound | Concentration (p.p.m.) | No. of diseased spots per leaf |
|---|---|---|---|
| 1 | 3,5-Cl₂-C₆H₃–N[C(=O)CH–S·CH₂·CH₃][C(=O)CH₂] | 500 | 3 |
| 2 | 3,5-Cl₂-C₆H₃–N[C(=O)CH·S·CH₂(CH₂)₂CH₃][C(=O)CH₂] | 500 | 0 |

Table 6-continued

| No. | Compound | Concentration (p.p.m.) | No. of diseased spots per leaf |
|---|---|---|---|
| 3 | 3,5-dichlorophenyl-N-(CO-CH(S-phenyl)-CO-CH₂) | 500 | 0 |
| 4 | 3,5-dichlorophenyl-N-(CO-CH(S-4-chlorophenyl)-CO-CH₂) | 500 | 6 |
| 5 | 3,5-dichlorophenyl-N-(CO-CH(SCH₂-phenyl)-CO-CH₂) | 500 | 8 |
| 6 | 3,5-dichlorophenyl-N-(CO-CH(N(CH₂CH₃)₂)-CO-CH₂) | 500 | 19 |
| 7 | 3,5-dichlorophenyl-N-(CO-CH(N-pyrrolidinyl)-CO-CH₂) | 500 | 26 |
| 8 | 3,5-dichlorophenyl-N-(CO-CH(N-morpholinyl)-CO-CH₂) | 500 | 25 |
| 9 | 3,5-dibromophenyl-N-(CO-CH(S-phenyl)-CO-CH₂) | 500 | 0 |
| | Reference compound | | |
| 10 | phenyl-N-(CO-CH(S-phenyl)-CO-CH₂) | 500 | 48 |
| | Untreated | — | 76 |

Table 7

| No. | Compound | Concentration (p.p.m.) | No. of diseased spots per leaf |
|---|---|---|---|
| 1 | succinimide N-(3,5-dichlorophenyl), with CH-CH₂-CH ring | 100 | 0.8 |
| 2 | succinimide N-(3,5-dibromophenyl), with CH-CH₂-CH ring | 100 | 1.2 |
| 3 | 2,2-dimethylsuccinimide N-(3,5-dichlorophenyl) (CH₃, CH₃ on one C, H₂C) | 100 | 1.0 |
| 4 | 2,2-dimethyl-cyclopropane-dicarboximide N-(3,5-dichlorophenyl) | 100 | 0 |
| 5 | 3,3-dimethyl cyclopropane-1,2-dicarboximide N-(3,5-dichlorophenyl) | 100 | 1.9 |
| 6 | 3,3-dimethyl cyclopropane-1,2-dicarboximide N-(3,5-dibromophenyl) | 100 | 3.4 |
| 7 | 3,3-dimethyl cyclopropane-1,2-dicarboximide N-(3,5-diiodophenyl) | 100 | 3.8 |
| 8 | Reference compound: succinimide N-phenyl | 100 | 50.1 |
| | Untreated | — | 52.3 |

Table 8

| No. | Compound | Concentration (%) | No. of diseased spots per leaf |
|---|---|---|---|
| 1 | glutarimide N-(3,5-dichlorophenyl) | 2 | 0 |
| 2 | glutarimide N-(3,5-dibromophenyl) | 2 | 4.2 |
| 3 | Reference compound: glutarimide N-phenyl | 2 | 55.3 |
| | Untreated | — | 52.9 |

Table 9

| No. | Compound | Concentration (%) | No. of diseased spots per leaf |
|---|---|---|---|
| 1 | N-(3,5-dichlorophenyl)phthalimide | 2 | 7.1 |
| 2 | N-(3,5-dichlorophenyl)tetrahydrophthalimide | 2 | 5.6 |
| 3 | N-(3,5-dibromophenyl)tetrahydrophthalimide | 2 | 9.2 |
| 4 | N-(3,5-dichlorophenyl)-1,2,3,6-tetrahydrophthalimide | 2 | 8.5 |

Table 9-continued

| No. | Compound | Concentration (%) | No. of diseased spots per leaf |
|---|---|---|---|
| 5 | [cyclohexane-fused imide with N-(3,5-dichlorophenyl)] | 2 | 4.3 |
| 6 | Reference Compound [phthalimide N-phenyl] | 2 | 78.1 |
| 7 | Reference compound [phthalimide N-(3-chlorophenyl)] | 2 | 59.8 |
| 8 | Reference compound [phthalimide N-(3-methylphenyl)] | 2 | 73.2 |
| 9 | Reference compound [tetrahydrophthalimide N-phenyl] | 2 | 70.4 |
| | Untreated | — | 76.9 |

Table 10

| No. | Compound | Concentration (%) | No. of diseased spots per leaf |
|---|---|---|---|
| 1 | $CH_3$-CH-CO, $CH_3$-CH-CO, N-(3,5-dichlorophenyl) | 2.0 | 0 |
| 2 | $CH_3$-CH-CO, $CH_3$-CH-CO, N-(3,5-dibromophenyl) | 2.0 | 0.9 |
| 3 | $CH_3$-CH-CO, $CH_3$-CH-CO, N-(3,5-diiodophenyl) | 2.0 | 1.8 |
| 4 | $CH_3$-CH-CO, $C_2H_5$-CH-CO, N-(3,5-dichlorophenyl) | 2.0 | 0.3 |
| 5 | Reference compound $CH_3$-CH-CO, $CH_3$-CH-CO, N-phenyl | 2.0 | 68.4 |
| 6 | Reference compound $CH_3$-CH-CO, $CH_3$-CH-CO, N-(3-chlorophenyl) | 2.0 | 56.2 |
| 7 | Reference compound $CH_3$-CH-CO, $CH_3$-CH-CO, N-(3,4-dichlorophenyl) | 2.0 | 60.1 |
| | Untreated | — | 67.3 |

Table 11

| No. | Compound | Concentration (%) | No. of diseased spots per leaf |
|---|---|---|---|
| 1 | Cl-CH-CO, $CH_2$-CO, N-(3,5-dichlorophenyl) | 2.0 | 0 |
| 2 | Br-CH-CO, $CH_2$-CO, N-(3,5-dichlorophenyl) | 2.0 | 0.8 |

Table 11-continued

| No. | Compound | Concentration (%) | No. of diseased spots per leaf |
|---|---|---|---|
| 3 | [3,5-dichlorophenyl with CH(Cl)-C(=O) and CH(Cl)-C(=O) ring] | 2.0 | 2.4 |
| 4 | [3,5-dibromophenyl with CH(Cl)-C(=O) and CH₂-C(=O) ring] | 2.0 | 1.1 |
| 5 | [3,5-dichlorophenyl with CH(Br)-C(=O) and CH(Br)-C(=O) ring] | 2.0 | 1.9 |
| 6 | Reference compound [4-chlorophenyl with CH(Cl)-C(=O) and CH(Cl)-C(=O) ring] | 2.0 | 60.9 |
| 7 | Reference compound [2,5-dichlorophenyl with CH(Cl)-C(=O) and CH(Cl)-C(=O) ring] | 2.0 | 54.6 |
| 8 | Reference compound [4-nitrophenyl with CH(Cl)-C(=O) and CH(Cl)-C(=O) ring] | 2.0 | 53.2 |
| 9 | Reference compound [phenyl with CH(Cl)-C(=O) and CH₂-C(=O) ring] | 2.0 | 70.7 |
| 10 | Reference compound [4-nitrophenyl with CH(Cl)-C(=O) and CH₂-C(=O) ring] | 2.0 | 58.1 |
| 11 | Reference compound [3-methylphenyl with CH(Cl)-C(=O) and CH₂-C(=O) ring] | 2.0 | 63.2 |
| Untreated | — | | 69.4 |

Table 12

| No. | Compound | Concentration (%) | No. of diseased spots per leaf |
|---|---|---|---|
| 1 | [3,5-dichlorophenyl-N with C(=O)-CH(SOCH₂CH₃) and C(=O)-CH₂ ring] | 2.0 | 0 |
| 2 | [3,5-dichlorophenyl-N with C(=O)-CH(SOCH₂(CH₂)₆CH₃) and C(=O)-CH₂ ring] | 2.0 | 3.5 |

Table 12-continued

| No. | Compound | Concentration (%) | No. of diseased spots per leaf |
|---|---|---|---|
| 3 | 3,5-dichlorophenyl-N-imide with –CH–SOCH$_2$(CH$_2$)$_2$CH$_3$ and –CH$_2$ substituents | 2.0 | 1.8 |
| 4 | 3,5-dichlorophenyl-N-imide with –CH–SOCH$_2$–phenyl and –CH$_2$ substituents | 2.0 | 0.3 |
| Untreated | | — | 66.7 |

TEST 3

Each of the test compounds in the form of emulsifiable concentrates was diluted with water and applied to rice plants, which had been cultured in pots of 9 cm. in diameter and grown up to 50–60 cm. in height, in a proportion of 10 ml. of the dilution per pot. After 3 hours, a mycelium-disc-inoculum of *Pellicularia sasakii* was applied onto the sheaths. 5 Days thereafter, the infectious state of the sheaths was observed, and the degree of damage was calculated according to the following equation:

$$\text{Degree of damage} = \frac{\sum \left( \begin{array}{c} \text{Infection} \\ \text{index} \end{array} \times \begin{array}{c} \text{Number of} \\ \text{stems} \end{array} \right)}{\text{Total number of stems} \times 3} \times 100$$

wherein the infection index was determined on the basis of the following criteria:

| Infection index | Infectious state |
|---|---|
| 0 | No infectious spots on the sheaths. |
| 1 | Infectious spot-like shades. |
| 2 | Infectious spots of less than 3 cm. in size. |
| 3 | Infectious spots of not less than 3 cm. in size. |

The results were as shown in the tables below, from which it is understood that the N-(3,5-dihalophenyl)imide compounds (I) are stronger in anti-fungal activity against Sheath blight of rice than compounds analogous thereto.

Table 13

| No. | Compound | Concentration (p.p.m.) | Degree of damage |
|---|---|---|---|
| 1 | 3,5-dichlorophenyl-N-imide with –CH–S–CH$_2$·CH$_3$ and –CH$_2$ substituents | 200 | 2.7 |
| 2 | 3,5-dichlorophenyl-N-imide with –CH–S–CH$_2$(CH$_2$)$_2$CH$_3$ and –CH$_2$ substituents | 200 | 0 |
| 3 | 3,5-dichlorophenyl-N-imide with –CH–S–phenyl and –CH$_2$ substituents | 200 | 0 |

Table 13-continued

| No. | Compound | Concentration (p.p.m.) | Degree of damage |
|---|---|---|---|
| 4 | 3,5-dichlorophenyl-N(COCH(S-4-chlorophenyl)-CH$_2$CO) | 200 | 1.8 |
| 5 | 3,5-dichlorophenyl-N(COCH(SCH$_2$-phenyl)-CH$_2$CO) | 200 | 3.9 |
| 6 | 3,5-dichlorophenyl-N(COCH(morpholino)-CH$_2$CO) | 200 | 18.9 |
| 7 | 3,5-dibromophenyl-N(COCH(S-phenyl)-CH$_2$CO) | 200 | 0 |
| 8 | Reference compound: phenyl-N(COCH(S-phenyl)-CH$_2$CO) | 200 | 86.9 |
| 9 | TUZ* | 200 | 3.6 |
|  | Untreated | — | 100 |

*TUZ contains 40% (by weight) of tetramethylthiuram disulfide, 20% (by weight) of methylarsine bis(dimethyldithiocarbamate) and 20% (by weight) of zinc dimethyldithiocarbamate.

Table 14

| No. | Compound | Concentration (p.p.m.) | Degree of damage |
|---|---|---|---|
| 1 | cyclopropane-1,2-dicarboximide N-(3,5-dichlorophenyl) | 200 | 8.9 |
| 2 | 2,2-dimethylcyclopropane-1,1-dicarboximide N-(3,5-dichlorophenyl) | 200 | 5.2 |
| 3 | 3,3-dimethylcyclopropane-1,2-dicarboximide N-(3,5-dichlorophenyl) | 200 | 0 |
| 4 | 3,3-dimethylcyclopropane-1,2-dicarboximide N-(3,5-dibromophenyl) | 200 | 13.4 |

Table 14-continued

| No. | Compound | Concentration (p.p.m.) | Degree of damage |
|---|---|---|---|
| 5 | Reference compound 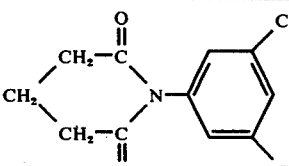 | 200 | 100 |
| 6 | TUZ | 200 | 4.7 |
| — | Untreated | — | 100 |

Table 15

| No. | Compound | Concentration (p.p.m.) | Degree of damage |
|---|---|---|---|
| 1 | 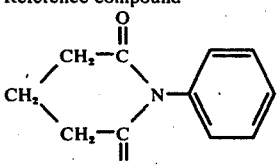 | 1,000 | 14.5 |
| 2 | Reference compound 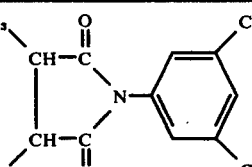 | 1,000 | 100 |
| — | Untreated | — | 100 |

Table 16

| No. | Compound | Concentration (p.p.m.) | Degree of damage |
|---|---|---|---|
| 1 | 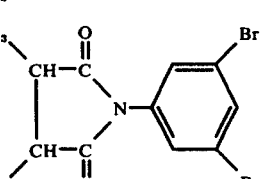 | 200 | 0.8 |
| 2 | 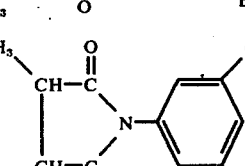 | 200 | 0 |
| 3 | 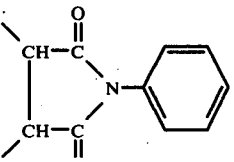 Reference compound | 200 | 2.8 |

Table 16-continued

| No. | Compound | Concentration (p.p.m.) | Degree of damage |
|---|---|---|---|
| 4 | 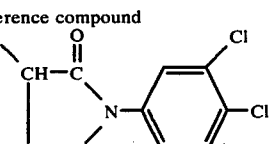 | 200 | 100 |
| 5 | Reference compound 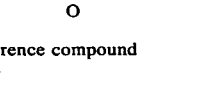 | 200 | 100 |
| 6 | Reference compound TUZ | 200 | 4.3 |
| — | Untreated | — | 100 |

Table 17

| No. | Compound | Concentration (p.p.m.) | Degree of damage |
|---|---|---|---|
| 1 | | 500 | 0 |
| 2 | | 500 | 3.6 |
| 3 | | 500 | 4.5 |
| 4 | Reference compound | 500 | 100 |
| 5 | Reference compound | 500 | 100 |

Table 17-continued

| No. | Compound | Concentration (p.p.m.) | Degree of damage |
|---|---|---|---|
| 6 | Cl-CH-C(=O)-N(-C(=O)-CH₂-)-phenyl | 500 | 100 |
| 7 | Reference compound<br>Cl-CH-C(=O)-N(-C(=O)-CH₂-)-(3-CH₃-phenyl) | 500 | 100 |
| 8 | Reference compound<br>TUZ | 500 | 3.7 |
| — | Untreated | — | 100 |

TEST 4

Farm soil was charged into pots of 9 cm. in diameter, and a soil (10 ml.) infected with *Pellicularia filamentosa* was dispersed over the surface of said soil. Each of the test compounds in the form of emulsifiable concentrates was diluted with water to a given concentration, and the dilution was applied into each pot in a proportion of 15 ml. per pot. After 2 hours, 10 seeds of cucumber were sowed therein. 5 Days thereafter, the infectious state of the grown seedlings was observed, and the percentage of stand was calculated according to the following equation:

$$\text{Percentage of stand} = \frac{\text{Number of healthy seedlings in treated plot}}{\text{Number of germinated seedlings in untreated and uninoculated plot}} \times 100$$

The results were as shown in the tables below, from which it is understood that the N-(3,5-dihalophenyl)imide compounds (I) are stronger in soil disinfectant activity than compounds analogous thereto.

Table 18

| No. | Compound | Concentration (p.p.m.) | Degree of degree |
|---|---|---|---|
| 1 | 3,5-diCl-phenyl-N(-C(=O)-CH-SOCH₂CH₃)(-C(=O)-CH₂) | 500 | 0 |
| 2 | 3,5-diCl-phenyl-N(-C(=O)-CH-SOCH₂(CH₂)₂CH₃)(-C(=O)-CH₂) | 500 | 3.6 |
| 3 | 3,5-diCl-phenyl-N(-C(=O)-CH-SOCH₂-phenyl)(-C(=O)-CH₂) | 500 | 0.4 |
| 4 | Reference compound<br>TUZ | 500 | 3.8 |
| — | Untreated | — | 100 |

Table 19

| No. | Compound | Concentration (p.p.m.) | Percentage of stand |
|---|---|---|---|
| 1 | 3,5-diCl-phenyl-N(-C(=O)-CH-S·CH₂·CH₃)(-C(=O)-CH₂) | 500 | 98.0 |

Table 19-continued

| No. | Compound | Concentration (p.p.m.) | Percentage of stand |
|---|---|---|---|
| 2 | 3,5-dichlorophenyl-N(C(=O)CH(SPh)-C(=O)CH₂) | 500 | 100 |
| 3 | 3,5-dichlorophenyl-N(C(=O)CH(S-4-ClC₆H₄)-C(=O)CH₂) | 500 | 97.6 |
| 4 | 3,5-dichlorophenyl-N(C(=O)CH(SCH₂Ph)-C(=O)CH₂) | 500 | 83.4 |
| 5 | 3,5-dichlorophenyl-N(C(=O)CH(N(CH₂CH₃)₂)-C(=O)CH₂) | 500 | 78.8 |
| 6 | 3,5-dibromophenyl-N(C(=O)CH(SPh)-C(=O)CH₂) | 500 | 91.0 |
| — | Untreated (Inoculated) | — | 0 |
| — | Untreated (Uninoculated) | — | 100 |

Table 20

| No. | Compound | Concentration (p.p.m.) | Percentage of stand |
|---|---|---|---|
| 1 | cyclopropane-dicarboximide-N-(3,5-dibromophenyl) | 1,000 | 93.8 |
| 2 | 2,2-dimethylcyclopropane-dicarboximide-N-(3,5-dichlorophenyl) | 1,000 | 100.0 |
| 3 | 2,2-dimethylcyclopropane-dicarboximide-N-(3,5-diiodophenyl) | 1,000 | 90.1 |
| 4 | cyclopropane-dicarboximide-N-phenyl (Reference compound) | 1,000 | 0 |

Reference compound

Table 20-continued

| No. | Compound | Concentration (p.p.m.) | Percentage of stand |
|---|---|---|---|
| 5 | pentachloronitrobenzene (Cl₅C₆NO₂) * | 1,000 | 93.7 |
| — | Untreated (Inoculated) | — | 0 |
| — | Untreated (Uninoculated) | — | 100.0 |

*Fungicide used as soil disinfectant.

Table 21

| No. | Compound | Concentration (p.p.m.) | Percentage of stand |
|---|---|---|---|
| 1 | N-(3,5-dichlorophenyl)-succinimide (dimethyl) | 500 | 92.5 |
| 2 | N-(3,5-dibromophenyl)-succinimide (dimethyl) | 500 | 88.7 |
| 3 | Reference compound: N-phenyl-succinimide (dimethyl) | 500 | 0 |
| 4 | Reference compound: pentachloronitrobenzene * | 500 | 90.4 |
| — | Untreated (Inoculated) | — | 0 |
| — | Untreated (Uninoculated) | — | 100 |

*Fungicide used as soil disinfectant.

Table 22

| No. | Compound | Concentration (p.p.m.) | Percentage of stand |
|---|---|---|---|
| 1 | N-(3,5-dichlorophenyl)-tetrahydrophthalimide | 500 | 87.8 |
| 2 | N-(3,5-dichlorophenyl)-dihydrophthalimide | 500 | 87.3 |
| 3 | N-(3,5-dichlorophenyl)-hexahydrophthalimide (H) | 500 | 90.2 |
| 4 | Reference compound: N-phenyl-tetrahydrophthalimide | 500 | 0 |
| 5 | Reference compound: pentachloronitrobenzene | 500 | 86.4 |
| — | Untreated (Inoculated) | — | 0 |
| — | Untreated (Uninoculated) | — | 100 |

Table 23

| No. | Compound | Concentration (p.p.m.) | Percentage of stand |
|---|---|---|---|
| 1 | N-(3,5-dichlorophenyl)-2,3-dimethylsuccinimide | 500 | 100 |
| 2 | N-(3,5-dibromophenyl)-2,3-dimethylsuccinimide | 500 | 97.3 |

Table 23-continued

| No. | Compound | Concentration (p.p.m.) | Percentage of stand |
|---|---|---|---|
| 3 | (CH₃)CH-C(=O)-N(-3,5-Cl₂C₆H₃)-CH(C₂H₅)-C(=O) | 500 | 98.4 |
| 4 | Reference compound (CH₃)CH-C(=O)-N(C₆H₅)-CH(CH₃)-C(=O) | 500 | 0 |
| 5 | Reference compound pentachloronitrobenzene | 500 | 88.6 |
| — | Untreated (Inoculated) | — | 0 |
| — | Untreated (Uninoculated) | — | 100 |

Table 24

| No. | Compound | Concentration (p.p.m.) | Percentage of stand |
|---|---|---|---|
| 1 | ClCH-C(=O)-N(-3,5-Cl₂C₆H₃)-CH₂-C(=O) | 500 | 98.5 |
| 2 | ClCH-C(=O)-N(-3,5-Br₂C₆H₃)-CH₂-C(=O) | 500 | 74.3 |
| 3 | BrCH-C(=O)-N(-3,5-Cl₂C₆H₃)-CHBr-C(=O) | 500 | 91.2 |
| 4 | Reference compound Cl₂CH-C(=O)-N(-2,5-Cl₂C₆H₃)-CHCl₂-C(=O) | 500 | 5.6 |
| 5 | Reference compound ClCH-C(=O)-N(C₆H₅)-CH₂-C(=O) | 500 | 0.8 |
| 6 | ClCH-C(=O)-N(-3-CH₃C₆H₄)-CH₂-C(=O) | 500 | 0 |
| 7 | Reference compound pentachloronitrobenzene | 500 | 96.6 |
| — | Untreated (Inoculated) | — | 0 |
| — | Untreated (Uninoculated) | — | 100 |

Table 25

| No. | Compound | Concentration (p.p.m.) | Percentage of stand |
|---|---|---|---|
| 1 | 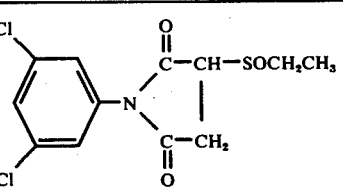 | 500 | 92.4 |

Table 25-continued

| No. | Compound | Concentration (p.p.m.) | Percentage of stand |
|---|---|---|---|
| 2 | [structure: 3,5-dichlorophenyl imide with CH—SOCH$_2$(CH$_2$)$_2$CH$_3$ and CH$_2$] | 500 | 87.3 |
| 3 | [structure: 3,5-dichlorophenyl imide with CH—SOCH$_2$—phenyl and CH$_2$] | 500 | 98.6 |
| 4 | Reference compound [pentachloronitrobenzene] | 500 | 94.3 |
| — | Untreated (Inoculated) | — | 0 |
| — | Untreated (Uninoculated) | — | 100 |

TEST 5

Each of the test compounds in the form of wettable powders was diluted with water to a given concentration and applied to pumpkin seedlings, which had been cultured in pots of 12 cm. in diameter and grown up to the 3–4 leaves stage, in a proportion of 7 ml. of the dilution per pot. After one day, the seedlings were inoculated by spraying with a spore suspension of *Sphaerotheca fulginea*. 10 Days thereafter, the infections state of the upper 4 leaves of the seedlings was observed, and the degree of damage was calculated from the infectious area according to the following equation.

$$\text{Degree of damage} = \frac{\Sigma \left( \begin{array}{c} \text{Infection index} \times \\ \text{Number of leaves} \end{array} \right)}{\text{Total number of leaves} \times 5} \times 100$$

wherein the infectious index was determined on the basis of the following criteria:

| Infection index | Infectious area |
|---|---|
| 0 | None |
| 1 | Small |
| 3 | Medium |
| 5 | Large |

The results were as shown in the tables below, from which it is understood that the N-(3,5-dihalophenyl)imide compounds (I) are stronger in anti-fungal activity (for powdery mildew) than compounds analogous thereto.

Table 26

| No. | Compound | Concentration (p.p.m.) | Degree of damage |
|---|---|---|---|
| 1 | [structure: 3,5-dichlorophenyl imide with two CH$_3$ groups] | 1,000 | 9.1 |
| 2 | [structure: phenyl imide with CH$_2$ bridge] | 1,000 | 41.7 |
| — | Untreated | — | 52.9 |

Table 27

| No. | Compound | Concentration (p.p.m.) | Degree of damage |
|---|---|---|---|
| 1 | [structure: tetrahydrophthalimide with 3,5-dichlorophenyl] | 500 | 2.3 |

Table 27-continued

| No. | Compound | Concentration (p.p.m.) | Degree of damage |
|---|---|---|---|
| 2 | [structure: tetrahydrophthalimide with 3,5-dibromophenyl] | 500 | 6.7 |
| 3 | [structure: hexahydrophthalimide with 3,5-dichlorophenyl] | 500 | 14.6 |
| 4 | Reference compound [structure: tetrahydrophthalimide with phenyl] | 500 | 45.8 |
| — | Untreated | — | 42.3 |

Table 28

| No. | Compound | Concentration (p.p.m.) | Degree of damage |
|---|---|---|---|
| 1 | [structure: diisopropyl succinimide with 3,5-dichlorophenyl] | 1,000 | 2.3 |
| 2 | Reference compound [structure: diisopropyl succinimide with phenyl] | 1,000 | 48.2 |
| — | Untreated | — | 56.3 |

Table 29

| No. | Compound | Concentration (p.p.m.) | Degree of damage |
|---|---|---|---|
| 1 | [structure: chloromethyl succinimide with 3,5-dichlorophenyl] | 1,000 | 0.8 |
| 2 | [structure: dichloro succinimide with 3,5-dichlorophenyl] | 1,000 | 2.3 |
| 3 | Reference compound [structure: chloromethyl succinimide with phenyl] | 1,000 | 40.2 |
| — | Untreated | — | 43.3 |

Table 30

| No. | Compound | Concentration (p.p.m.) | Degree of damage |
|---|---|---|---|
| 1 | [structure: 3,5-dichlorophenyl succinimide with CH-SO-CH$_2$-phenyl substituent] | 1,000 | 6.3 |
| — | Untreated | — | 58.4 |

TEST 6

Anti-fungal spectrum:

By means of the agar dilution method, the growth-inhibiting effects of the N-(3,5-dihalophenyl)imide compounds (I) on various phytopathogenic fungi were investigated. As typical test results, there are shown in the table below those of N-(3',5'-dichlorophenyl)cyclopropanedicarboximide.

Table 31

| Test fungi | Minimum concentration of inhibition (p.p.m.) |
|---|---|
| Pyricularia cryzae | 200 |
| Pellicularia filamentosa | 40 |
| Botrytis cinerea | 8 |
| Sclerotinia sclerotiorum | 40 |
| Alternaria kikuchiana | 40 |
| Alternaria mali | 40 |
| Glomerella cingulata | 200 |

TEST 7

By means of a method similar to that as in Test 6, the growth-inhibiting effects of N-(3',5'-dichlorophenyl)-cyclopropanedicarboximide on *Aspergillus niger* ATCC 9642, which propagates on industrial products, were investigated to obtain the results set forth in the table below.

Table 32

| No. | Compound | Minimum concentration of inhibition (p.p.m.) |
|---|---|---|
| 1 | [structure: cyclopropane-dicarboximide with 3,5-dichlorophenyl] | 2,000 |
| 2 | Reference compound [structure: cyclopropane-dicarboximide with phenyl] | 2,000< |

Note: "2000<" means no activity at 2000 p.p.m.

TEST 8

Anti-fungal spectrum:

By means of the agar dilution method, the growth-inhibiting effects of N-(3,5-dichlorophenyl)glutaric acid imide on various phytopatogenic fungi were investigated to obtain the results as set forth in the table below.

Table 33

| Test fungi | Minimum concentration of inhibition (p.p.m.) |
|---|---|
| *Cochliobolus miyabeanus* | 200 |
| *Pellicularia filamentosa* | 200 |
| *Botrytis cinerea* | 40 |
| *Sclerotinia sclerotiorum* | 40 |
| *Alternaria kikuchiana* | 200 |
| *Alternaria mali* | 200 |

TEST 9

Effects of controlling *Aspergillus niger* ATCC 9642:

By means of a method similar to that as in Test 8, the growth-inhibiting effects of N-(3,5-dichlorophenyl)-glutarimide on *Aspergillus niger* ATCC 9642 were investigated to obtain the results as set forth in the table below.

Table 34

| Compound | Minimum concentration of inhibition (p.p.m.) |
|---|---|
| [structure: glutarimide with 3,5-dichlorophenyl] | 5,000 |
| [structure: glutarimide with 3,5-dibromophenyl] | 5,000 |
| Reference compound [structure: glutarimide with phenyl] | 5,000< |

Note: "5000<" means no activity at 5000 p.p.m.

TEST 10

Anti-fungal spectrum:

By means of the agar dilution method, the growth-inhibiting effects of N-(3,5-dichlorophenyl)-α-chlorosuccinimide on various phytopathogenic fungi were invetigated to obtain the results as set forth in the following table.

Table 35

| Test fungi | Minimum concentration of inhibition (p.p.m.) |
|---|---|
| *Pyricularia oryzae* | 200 |
| *Pellicularia filamentosa* | 200 |
| *Corticium rolfsii* | 200 |
| *Botrytis cinerea* | 200 |
| *Sclerotinia sclerotiorum* | 200 |
| *Glomerella cingulata* | 200 |

TEST 11

Effects of controlling *Aspergillus niger* ATCC 9642:

By means of a method similar to that as in Test 10, the growth-inhibiting effects of N-(3,5-dichlorophenyl)-α-chlorosuccinimide on *Aspergillus niger*, which propagates on industrial products, were investigated to obtain the result as set forth in the following table:

Table 36

| Test compound | Minimum concentration of inhibition (p.p.m.) |
|---|---|
| [structure: α-chlorosuccinimide with 3,5-dichlorophenyl] | 1,000 |

TEST 12

Anti-fungal spectrum:

By means of the agar dilution method, the growth-inhibiting effects of N-(3,5-dichlorophenyl)-ethylsulfinylsuccinimide (compound 1) and N-(3,5-dichlorophenyl)-n-btylsulfinylsuccinimide (compound 2) on various phytopathogenic bacteria and fungi were investigated to obtain the results as set forth in the following table:

Table 37

| Test organism | Minimum concentration of inhibition (p.p.m.) | |
|---|---|---|
| | Compound (1) | Compound (2) |
| *Pyricularia oryzae* | 200 | 200 |
| *Xanthomonas oryzae* | 200 | 200 < |
| *Pellicularia filamentosa* | 200 | 200 |
| *Pythium aphanidermatum* | 200 | 200 < |
| *Botrytis cinerea* | 200 | 40 |
| *Sclerotinia sclerotiorum* | 200 | 200 |
| *Alternaria kikuchiana* | 200 | 40 |
| *Glomerella cingulata* | 200 | 40 |
| *Cochliobolus miyabeanus* | 200 | 200 |
| *Helminthosporium sigmoideum* | 200 | |
| *Fusarium pisi* | 200 | |
| *Xanthomonas pruni* | 200 | 200 < |
| *Xanthomonas citri* | 200 | 200 |
| *Erwinia aroidae* | 200 | 200 < |

TEST 13

Effects of controlling *Aspergillus niger* ATCC 9642:

By means of a method similar to that as in Test 12, the growth-inhibiting effects of N-(3,5-dichlorophenyl)ethylsulfinylsuccinimide and N-(3,5-dichlorophenyl)-n-butylslfinylsucciniimide on *Aspergillus niger* ATCC 9642 were investigated to obtain the results as set forth in the following table:

Table 38

| Compound | Minimum concentration of inhibition (p.p.m.) |
|---|---|
| [structure: 3,5-dichlorophenyl-N-succinimide with –CH–SOCH$_2$(CH$_2$)$_2$CH$_3$] | 200 |
| [structure: 3,5-dichlorophenyl-N-succinimide with –CH–SOCH$_2$(CH$_2$)$_2$CH$_3$] | 200 |

As clearly understood from the above description, the N-(3,5-dihalophenyl)imide compounds (I) are useful as anti-microbial agents, particularly as agricultural and industrial and sometimes, pharmaceutical field. In other words, they may be used as agricultural chemicals for prevention or inhibition of plant diseases caused by phytopathogenic fungi and bacteria. They may be used also as industrial chemicals for preventing or inhibiting industrial products from staining.

For the above purpose, the N-(3,5-dihalophenyl)imide compounds (I) may be used as they are but, in most practical cases, they are extended with a suitable carrier(s) to bring them into the forms of conventional fungicides such as dusts, wettable powders, oil sprays, aerosols, tablets, emulsifiable concentrates, pellets, granules, ointment or powder. These anti-microbial compositions may contain, in addition to the N-(3,5-dihalophenyl)imide compounds (I) one or more of known fungicides, insecticides and herbicides such as, for example, Blasticidin S, Kasugamycin, Polyoxyn, Cellocidin, Chloramphenicol, O,O-diethyl-S-benzylphosphorothiolate, O-ethyl-S,S-diphenylphosphorodithiolate, O-n-butyl-S-ethyl-S-benzylphosphorodithiolate, O,O-diisopropyl-S-benzylphosphorothiolate, O-ethyl-S-benzylphenylthiophosphonate, pentachlorobenzaldoxime, pentachlorobenzyl alcohol, pentachloromandelonitrile, pentachlorohenyl acetate, iron methylarsonate, ferric ammonium methylarsonate, γ-1,2,3,4,5,6-hexachlorocyclohexane, 1,1,1-trichloro-2,2-bis(p-chlorophenyl)-ethane, O,O-dimethyl-O-(p-nitrophenyl) phosphorothioate, S-[1,2-bis(ethoxycarbonyl)ethyl] O,O-dimethyl phosphorodithioate, O-ethyl-O-p-nitrophenyl phenylphosphonothioate, α-naphthyl N-methylcarbamate, O,O-dimethyl-O-(p-nitro-m-methylphenyl) phosphorothioate, 3,4,5,6-tetrahydrophthalimide methyl chrysanthemate, 3,4-dimethylphenyl N-methylcarbamate, O,O-diethyl-O-(2-isopropyl-6-methyl-4-pyrimidinyl) thiophosphate, O,O-dimethyl-2,2-dichlorovinyl phosphate, 1,1-bis(p-chlorophenyl)-2,2,2-trichloroethanol, 1,2-dibromoethane, 1,2-dibromo-3-chloropropane, zinc ethylene-bis(dithiocarbamate), manganese ethylene-bis(dithiocarbamate), 2,3-dichloro-1,4-naphthoquinone, N-(trichloromethylthio)-4-cyclohexene-1,2-dicarboximide, N-(1,1,2,2-tetrachloroethylthio)-4-cyclohexene-1,2-dicarboximide, 6-methyl-2,3-quinoxaline dithiol cyclic carbonate, tetrachloroisophthalonitrile, sodium p-dimethylaminobenzene diazosulfonate, 2,4-dichloro-6-(2-chloroanilino)-S-triazine, 2,4-dichlorophenoxyacetic acid, 4-chloro-2-methylphenoxyacetic acid, 3,4-dichloropropionanilide, 2,4-dichlorophenyl-4'-nitrophenyl ether, 2-chloro-4,6-bis(ethylamino)-S-triazine, sodium N-(1-naphthyl) phthalamate, etc. The anti-microbial compositions may also contain one or more of materials known to be active as nematocides, acaricides, fertilizers, soil conditioners, soil disinfectants and plant growth regulators. Examples of typical anti-microbial compositions according to the present invention are as follows:

a. Dusts obtained by dispersing at least one of the N-(3,5-dichlorophenyl)imide compounds (I) as active ingredient to a concentration of 0.1 to 50% by weight in an inert carrier, e.g. talc, diatomaceous earth, wood flour or clay.

b. Wettable powders obtained by dispersing at least one of the N-(3,5-dichlorophenyl)imide compounds (I) as active ingredient to a concentration of 0.1 to 95%, preferable 0.1 to 80%, by weight in an inert adsorbent carrier, e.g. diatomaceous earth, together with a wetting and/or dispersing agent such as an alkali metal salt of a long aliphatic sulfate chain, a partly neutralized sulfuric acid derivative of either a petroleum oil or a natural occurring glyceride or a condensation product of an alkylene oxide with an organic acid.

c. Emulsifiable concentrates obtained by dispersing at least one of the N-(3,5-dichlorophenyl)imide compounds (I) as active ingredient to a concentration of 0.1 to 50% by weight in an organic solvent, e.g. dimethyl sulfoxide, plus an emulsifier such as an alkali metal salt of a long aliphatic sulfate chain, a partly neutralized sulfuric acid derivative of either a petroleum oil or a natural occurring glyceride or a condensation product of an alkylene oxide with an organic acid.

d. Compositions of the N-(3,5-dichlorophenyl)imide compounds (I) formulated in the manner commonly employed in the art for the preparation of microbicidal granules, dusts and aerosols.

Practical and presently-preferred embodiments of the present invention are illustratively shown below with reference to examples, in which parts and percentages are by weight.

Examples 1–59 are connected with the syntheses of the present compounds.

EXAMPLE 1–13

Standard operational process for the syntheses of the present compounds:

A mixture comprising 0.1 mole of N-(3,5-dihalophenyl)succinamic acid, 50 ml. of acetic anhydride and 1 g. of anhydrous sodium acetate is fed to a 100 ml. four-necked flask and is heated with stirring at 100° C. for 1 hour. Thereafter, the acetic acid and acetic anhydride are removed by distillation under reduced pressure, and the residue is washed with water and dried, whereby a desired N-(3,5-dihalophenyl)succinimide is obtained in a favorable yield. If necessary, recrystallization from ethanol is effected to obtain the desired product in a pure form.

The N-phenylsuccinamic acid employed in the present process is easily obtainable according to an ordinary procedure from a corresponding succinic anhydride derivative and an aniline derivative. Typical examples of the succinic anhydride and aniline are as set forth below, but it is needless to say that the scope of the present invention is not limited thereby.

Succinic anhydrides:

2-Methylthio succinic anhydride
2-Ethylthio succinic anhydride
2-n-Propylthio succinic anhydride
2-iso-Propylthio succinic anhydride
2-n-Butylthio succinic anhydride
2-iso-Butylthio succinic anhydride
2-sec-Butylthio succinic anhydride
2-tert-Butylthio succinic anhydride
2-n-Amylthio succinic anhydride
2-iso-Amylthio succinic anhydride
2-tert-Amylthio succinic anhydride
2-Hexylthio succinic anhydride
2-Heptylthio succinic anhydride
2-Octylthio succinic anhydride
2-Nonylthio succinic anhydride
2-Decylthio succinic anhydride
2-Phenylthio succinic anhydride
2-(o-Chlorophenylthio) succinic anhydride
2-(m-Chlorophenylthio) succinic anhydride
2-(p-Chlorophenylthio) succinic anhydride
2-(o-Methylphenylthio) succinic anhydride
2-(m-Methylphenylthio) succinic anhydride
2-(p-Methylphenylthio) succinic anhydride
2-(p-Nitrophenylthio) succinic anhydride
2-Benzylthio succinic anhydride
2-Dimethylamino succinic anhydride
2-(Di-n-propylamino) succinic anhydride
2-(Di-iso-propylamino) succinic anhydride
2-(Di-n-butylamino) succinic anhydride
2-(Di-iso-butylamino) succinic anhydride
2-(Di-n-amylamino) succinic anhydride
2-(Di-iso-amylamino) succinic anhydride
2-Dihexylamino succinic anhydride
2-Pyrrolidino succinic anhydride
2-Piperidino succinic anhydride
2-Morpholino succinic anhydride Anilines:

3,5-Difluoroaniline
3,5-Dichloroaniline
3,5-Dibromoaniline
3,5-Diiodoaniline

Syntheses were effected according to the abovementioned operational process to obtain the results as shown in the following table:

Table 39

| Ex. ample No. | Succinamic acid | Obtained N-(3,5-dihalophenyl)-imide compound |||||||
|---|---|---|---|---|---|---|---|---|
| | | Structural formula | Yield (%) | Physical constant (°C) | Elementary analysis (X: halogen atom) ||||
| | | | | | C (%) | H (%) | N (%) | X (%) |
| 1 | $CH_3CH_2S$-CHCOOH / $CH_2CONH$-(3,5-diCl-phenyl) or $CH_3CH_2S$-CH(CH_2COOH)-CHCONH-(3,5-diCl-phenyl) | N-(3,5-dichlorophenyl) imide with -CHSCH$_2$CH$_3$ | 95 | m.p. 104–106 | Calculated: 47.38  Found: 47.25 | 3.64  3.70 | 4.60  4.53 | (Cl) 23.31  23.25 |
| 2 | $CH_3(CH_2)_2S$-CHCOOH / $CH_2CONH$-(3,5-diCl-phenyl) or $CH_3(CH_2)_2CH_2S$-CHCONH-(3,5-diCl-phenyl) with $CH_2COOH$ | N-(3,5-dichlorophenyl) imide with -CHSCH$_2$(CH$_2$)$_2$CH$_3$ | 93 | m.p. 60–61.5 | Calculated: 50.61  Found: 50.52 | 4.55  4.43 | 4.22  4.25 | (Cl) 21.34  21.44 |
| 3 | $CH_3(CH_2)_6S$-CHCOOH / $CH_2CONH$-(3,5-diCl-phenyl) or $CH_3(CH_2)_6CH_2S$-CHCONH-(3,5-diCl-phenyl) with $CH_2COOH$ | N-(3,5-dichlorophenyl) imide with -CHSCH$_2$(CH$_2$)$_6$CH$_3$ | 96 | m.p. 47–51 | Calculated: 55.67  Found: 55.60 | 5.97  5.90 | 3.61  3.72 | (Cl) 18.26  18.50 |
| 4 | C$_6$H$_5$S-CHCOOH / CH$_2$CONH-(3,5-diCl-phenyl) or C$_6$H$_5$-S-CH(CH$_2$COOH)-CHCONH-(3,5-diCl-phenyl) | N-(3,5-dichlorophenyl) imide with -CH-S-C$_6$H$_5$ | 95 | m.p. 150–151 | Calculated: 54.56  Found: 54.70 | 3.15  3.20 | 3.98  3.85 | (Cl) 20.13  20.03 |
| 5 | (4-Cl-C$_6$H$_4$)-S-CHCOOH / CH$_2$CONH-(3,5-diCl-phenyl) or (4-Cl-C$_6$H$_4$)-S-CH(CH$_2$COOH)-CH-CONH-(3,5-diCl-phenyl) | N-(3,5-dichlorophenyl) imide with -CH-S-(4-Cl-C$_6$H$_4$) | 90 | m.p. 119–120.5 | Calculated: 49.70  Found: 49.54 | 2.61  2.50 | 3.62  3.75 | (Cl) 27.51  27.85 |

Table 39-continued

| | | Obtained N-(3,5-dihalophenyl)-imide compound | | | | | |
|---|---|---|---|---|---|---|---|
| Example No. | Succinamic acid | Structural formula | Yield (%) | Physical constant (°C) | \multicolumn{4}{c}{Elementary analysis (X: halogen atom)} |
| | | | | | C (%) | H (%) | N (%) | X (%) |
| 6 | 4-CH₃-C₆H₄-S-CH(COOH)-CH₂-CONH-(3,5-diCl-C₆H₃) or 4-CH₃-C₆H₄-S-CH(CH₂COOH)-CONH-(3,5-diCl-C₆H₃) | N-(3,5-dichlorophenyl) imide with CH-S-C₆H₄-CH₃ substituent | 91 | m.p. 145–147 | Calculated: 55.75  Found: 55.82 | 3.58  3.35 | 3.82  3.78 | (Cl) 19.36  19.51 |
| 7 | C₆H₅-CH₂-S-CH(COOH)-CH₂-CONH-(3,5-diCl-C₆H₃) or C₆H₅-CH₂-S-CH(CH₂COOH)-CONH-(3,5-diCl-C₆H₃) | N-(3,5-dichlorophenyl) imide with CH-SCH₂-C₆H₅ substituent | 94 | b.p. 0.1 mmHg 197–200 | Calculated: 55.74  Found: 55.60 | 3.58  3.43 | 3.82  3.90 | (Cl) 19.36  19.55 |
| 8 | (CH₃CH₂)₂N-CH(COOH)-CH₂-CONH-(3,5-diCl-C₆H₃) or (CH₃CH₂)₂N-CH(CH₂COOH)-CONH-(3,5-diCl-C₆H₃) | N-(3,5-dichlorophenyl) imide with CH-N(CH₂CH₃)₂ substituent | 95 | m.p. 95–96.5 | Calculated: 53.35  Found: 53.23 | 5.12  5.05 | 8.89  8.93 | (Cl) 22.50  22.64 |
| 9 | [CH₃(CH₂)₂CH₂]₂N-CH(COOH)-CH₂-CONH-(3,5-diCl-C₆H₃) or [CH₃(CH₂)₂CH₂]₂N-CH(CH₂COOH)-CONH-(3,5-diCl-C₆H₃) | N-(3,5-dichlorophenyl) imide with CH-N[CH₂(CH₂)₂CH₃]₂ substituent | 93 | m.p. 89–91 | Calculated: 58.22  Found: 58.15 | 6.52  6.67 | 7.54  7.42 | (Cl) 19.10  19.00 |
| 10 | pyrrolidinyl-CH(COOH)-CH₂-CONH-(3,5-diCl-C₆H₃) or pyrrolidinyl-CH(CH₂COOH)-CONH-(3,5-diCl-C₆H₃) | N-(3,5-dichlorophenyl) imide with CH-N(pyrrolidinyl) substituent | 97 | m.p. 85–87 | Calculated: 53.69  Found: 53.80 | 4.51  4.40 | 8.95  8.78 | (Cl) 22.64  22.76 |

Table 39-continued

| Ex. ample No. | Succinamic acid | Structural formula | Yield (%) | Physical constant (°C) | Elementary analysis (X: halogen atom) | | | |
|---|---|---|---|---|---|---|---|---|
| | | | | | C (%) | H (%) | N (%) | X (%) |
| 11 | 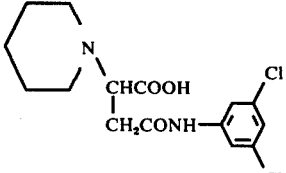 | 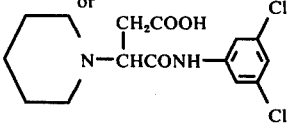 | 90 | m.p. 118–121 | Calculated: 55.06 Found: 55.22 | 4.93 5.05 | 8.56 8.42 | (Cl) 21.67 21.32 |
| 12 | 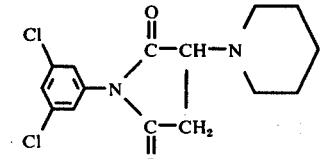 | 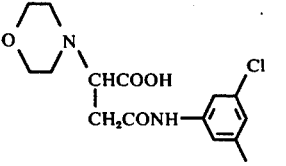 | 95 | m.p. 209–210 | Calculated: 51.08 Found: 51.19 | 4.29 4.13 | 8.51 8.27 | (Cl) 21.54 21.31 |
| 13 | 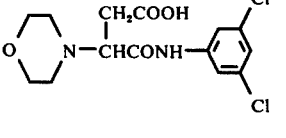 | 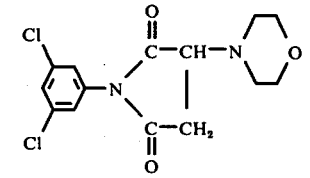 | 95 | m.p. 159.5–161 | Calculated: 43.56 Found: 43.26 | 2.51 2.47 | 3.18 3.30 | (Br) 36.23 36.44 |

EXAMPLE 14-20

Standard operational process:

A mixture comprising 0.1 mole of an N-phenylcyclopropanedicarboxylic acid monoamide derivative, 50 g. of acetic anhydride and 1 g. of anhydrous sodium acetate is fed to a 100 ml. four-necked flask and is heated with stirring at 100° C. for 30 minutes. Thereafter, the acetic acid and acetic anhydride are removed by distillation under reduced pressure, and the residue is washed with water and then dried, whereby a desired N-phenylcyclopropane dicarboximide derivative represented by the formula (I) is obtained in a favorable yield. If necessary, recrystallization from ethanol is effected to obtain the desired product in a pure form.

The N-phenylcyclopropane dicarboxylic acid monoamide derivative employed in the above process are easily obtainable according to an ordinary procedure from a corresponding cyclopropanedicarboxylic anhydride and an aniline. Typical examples of the cyclopropanedicarboxylic anhydride and aniline are as set forth below, but it is needless to say that the scope of the present invention is not limited thereby.

Anhydrides:

Cyclopropanedicarboxylic anhydride
1-Methylcyclopropanedicarboxylic anhydride
3-Methylcyclopropanedicarboxylic anhydride
1,2-Dimethylcyclopropanedicarboxylic anhydride
1,3-Dimethylcyclopropanedicarboxylic anhydride
3,3-Dimethylcyclopropanedicarboxylic anhydride
1,3,3-Trimethylcyclopropanedicarboxylic anhydride
1,2,3,3-Tetramethylcyclopropanedicarboxylic anhydride Anilines:

3,5-Dichloroaniline
3,5-Dibromoaniline
3,5-Diiodoaniline
3,5-Difluoroaniline

Results obtained by practicing the above-mentioned standard operational process are set forth in the table below.

Table 40

| Ex. No. | N-Phenyl cyclopropane dicarboxylic acid monoamide | Structural formula | Yield (%) | Melting point (°C) | Elementary analysis (X: halogen atom) | | | |
|---|---|---|---|---|---|---|---|---|
| | | | | | C(%) | H(%) | N(%) | X(%) |
| 14 | N-(3',5'-dichlorophenyl) cyclopropane dicarboxylic acid monoamide | | 96 | 130.5–132.0 | Calculated: 51.59 Found: 51.38 | 2.76 2.41 | 5.47 5.38 | (Cl) 27.69 27.61 |
| 15 | N-(3',5'-dibromophenyl) cyclopropane dicarboxylic acid monoamide | | 93 | 133.5–135.0 | Calculated: 38.29 Found: 37.99 | 2.05 1.82 | 4.06 4.27 | (Br) 46.33 46.57 |
| 16 | 1,2-dimethyl-N-(3',5'-dichlorophenyl)cyclopropane dicarboxylic acid monoamide | | 98 | 165.0–167.0 | Calculated: 54.95 Found: 55.08 | 3.90 3.72 | 4.93 4.68 | (Cl) 24.96 24.75 |
| 17 | 1,3- or 2,3-dimethyl-N-(3',5'-dichlorophenyl)cyclopropane dicarboxylic acid monoamide | | 97 | 127.5–129.5 | Calculated: 54.95 Found: 55.00 | 3.90 3.81 | 4.93 4.74 | (Cl) 24.96 24.99 |
| 18 | 3,3-dimethyl-N-(3',5'-dichlorophenyl)cyclopropane dicarboxylic acid monoamide | | 97 | 134.5–137.0 | Calculated: 54.95 Found: 54.83 | 3.90 3.76 | 4.93 5.12 | (Cl) 24.96 25.14 |
| 19 | 1,3- or 2,3-dimethyl-N-(3',5'-dibromophenyl) cyclopropane dicarboxylic acid monoamide | | 95 | 161.0–162.5 | Calculated: 41.85 Found: 41.92 | 2.97 3.04 | 3.76 3.65 | (Br) 42.84 42.93 |
| 20 | 1,3- or 2,3-dimethyl-N-(3',5'-diiodophenyl)cyclopropane dicarboxylic acid monoamide | | 98 | 170–172 | Calculated: 33.43 Found: 33.58 | 2.37 2.15 | 3.00 2.92 | (I) 54.34 54.61 |

EXAMPLE 21

N-(3,5-Dichlorophenyl) glutarimide:

A mixture comprising 27.6 g. of N-(3,5-dichlorophenyl) glutaric acid monoamide, 50 g. of acetic anhydride and 1 g. of anhydrous sodium acetate was fed to a 100 ml. four-necked flask and was heated with stirring at 80° – 90° C. for 1 hour. Thereafter, the acetic acid and acetic anhydride were removed by distillation under reduced pressure, and the residue was washed with water and then dried to obtain 24.8 g. of the above-mentioned compound in the form of white crystals, m.p. 172.5° – 174.5° C.

Elementary analysis:

| | C (%) | H (%) | N (%) | Cl (%) |
|---|---|---|---|---|
| Calculated | 51.19 | 3.51 | 5.43 | 27.47 |

-continued

Elementary analysis:

| | C (%) | H (%) | N (%) | Cl (%) |
|---|---|---|---|---|
| | | (for $C_{11}H_9O_2NCl_2$) | | |
| Found | 51.22 | 3.24 | 5.49 | 27.47 |

EXAMPLE 22

N-(3,5-Dibromophenyl) glutarimide:

36.5 g. of N-(3,5-dibromophenyl) glutaric acid monoamide was fed to a 50 ml. Claisen type distillation flask and was heated at 170° – 180° C. for 30 minutes, and the water formed was removed by distillation. The resulting crude product was recrystallized from a mixed ethanolbenzene solvent to obtain 28.4 g. of the above-mentioned compound in the form of white crystals, m.p. 151.5° – 153.5° C.

Elementary analysis:

| | C (%) | H (%) | N (%) | Br (%) |
|---|---|---|---|---|
| Calculated | 38.07 | 2.62 | 4.06 | 46.06 |
| | | (for $C_{11}H_9O_2NBr_2$) | | |
| Found | 37.94 | 2.66 | 4.13 | 46.09 |

EXAMPLE 23

N-(3,5-Diiodophenyl) glutarimide:

A mixture comprising 23.0 g. of N-(3,5-diiodophenyl) glutaric acid monoamide, 50 g. of acetic anhydride and 1 g. of anhydrous sodium acetate was fed to a 100 ml. four-necked flask and heated with stirring at 80° – 90° C. for 1 hour. Thereafter, the acetic acid and acetic anhydride were removed by distillation under reduced pressure, and the residue was washed with water and then dried to obtain 21.2 g. of the above-mentioned compound in the form of white crystals, m.p. 177° – 178.5° C.

Elementary analysis:

| | C (%) | H (%) | N (%) | I (%) |
|---|---|---|---|---|
| Calculated | 29.96 | 2.06 | 3.18 | 57.55 |
| | | (for $C_{11}H_9O_2NI_2$) | | |
| Found | 29.81 | 2.32 | 3.16 | 57.39 |

EXAMPLES 24–28

Standard operational procedures:

A mixture comprising 0.1 mole of an N-phenylphthalic acid monoamide derivative, 50 g. of acetic anhydride and 1 g. of anhydrous sodium acetate is fed to a 100 ml. four-necked flask and was heated with stirring at 80° – 100° C. for 1 hour. Thereafter, the acetic acid and acetic anhydride are removed by distillation under reduced pressure, and the residue is washed with water and is then dried, whereby a desired N-phenylphthalimide derivative represented by the formula (I) is obtained in a favorable yield. If necessary, recrystallization from ethanol is effected to obtain the desired product in a pure form.

The N-phenylphthalic acid monoamide derivative employed as the starting material in the above-mentioned standard operational process can be easily prepared according to an ordinary procedure from a phthalic anhydride and an aniline. Typical examples of the phthalic anhydride and aniline used in the above-mentioned process are as set forth below, but it is needless to say that the scope of the present invention is not limited thereby.

Phthalic anhydrides:

1,2-Dihydrophthalic anhydride
1,4-Dihydrophthalic anhydride
1,6-Dihydrophthalic anhydride
3,4-Dihydrophthalic anhydride
3,6-Dihydrophthalic anhydride
4,5-Dihydrophthalic anhydride
1,2,3,4-Tetrahydrophthalic anhydride
1,2,3,6-Tetrahydrophthalic anhydride
1,4,5,6-Tetrahydrophthalic anhydride
3,4,5,6-Tetrahydrophthalic anhydride
Hexahydrophthalic anhydride Anilines:

3,5-Difluoroaniline
3,5-Dichloroaniline
3,5-Dibromoaniline
3,5-Diiodoaniline

Results obtained by practicing the above-mentioned standard operational process are set forth in the following table:

Table 41

| | | Obtained N-(3,5-dihalophenyl)-imide compound | | | Elementary analysis (X:halogen atom) | | | |
|---|---|---|---|---|---|---|---|---|
| Example No. | Phthalic acid monoanilide | Structural formula | Melting Point (° C) | Yield (%) | C (%) | H (%) | N (%) | X (%) |
| 24 | (structure with COOH, CONH, Cl, Cl) | (imide structure with Cl, Cl) | 96–97 | 96 | Calculated: 56.78 Found: 57.03 | 3.74 3.50 | 4.73 4.66 | (Cl) 23.94 23.71 |
| 25 | (structure with COOH, CONH, Cl, Cl) | (imide structure with Cl, Cl) | 174–176 | 94 | Calculated: 57.17 Found: 57.32 | 3.08 2.98 | 4.76 4.56 | (Cl) 24.11 23.88 |

Table 41-continued

| Example No. | Phthalic acid monoanilide | Obtained N-(3,5-dihalophenyl)-imide compound | | | Elementary analysis (X:halogen atom) | | | |
|---|---|---|---|---|---|---|---|---|
| | | Structural formula | Melting Point (°C) | Yield (%) | C (%) | H (%) | N (%) | X (%) |
| 26 | (structure with COOH, CONH-phenyl-Cl,Cl) | (imide structure with Cl,Cl) | 204–205 | 97 | Calculated: 57.56  Found: 57.52 | 2.42  2.30 | 4.80  4.42 | (Cl) 24.27  23.41 |
| 27 | (structure with H, COOH, CONH-phenyl-Cl,Cl) | (imide structure with H, Cl,Cl) | 112.5 –115 | 95 | Calculated: 56.39  Found: 56.66 | 4.39  4.01 | 4.70  4.56 | (Cl) 23.78  23.37 |
| 28 | (cyclohexene with COOH, CONH-phenyl-Br,Br) | (imide structure with Br,Br) | 112– 115 | 93 | Calculated: 43.67  Found: 43.58 | 2.88  2.97 | 3.64  3.71 | (Br) 41.51  41.56 |

EXAMPLES 29–32

Standard operational process:

A mixture comprising 0.1 mole of an N-(3,5-dihalophenyl) succinic acid monoamide, 50 ml. of acetic anhydride and 1 g. of anhydrous sodium acetate is fed to a 100 ml. four-necked flask and is heated with stirring at 80° – 100° C. for 1 hour. Thereafter, the acetic acid and acetic anhydride are removed by distillation under reduced pressure, and the residue is washed with water and then dried, whereby a desired N-(3,5-dihalophenyl) succinimide derivative represented by the formula (I) is obtained in a favorable yield. If necessary, recrystallization from ethanol is effected to obtain the desired product in a pure form.

The N-(3,5-dihalophenyl) succinic acid monoamide derivative employed in the above-mentioned process is easily synthesized according to an ordinary procedure from a corresponding succinic anhydride and an aniline.

Typical examples of the succinic anhydride and aniline are as set forth below, but it is needless to say that the scope of the present invention is not limited thereby.

Succinic anhydrides:

2,3-Dimethylsuccinic anhydride
2-Ethyl-3-methylsuccinic anhydride
2,3-Diethylsuccinic anhydride
2-Methyl-3-propylsuccinic anhydride
2,3-Dipropylsuccinic anhydride Anilines:

3,5-Difluoroaniline
3,5-Dichloroaniline
3,5-Dibromoaniline
3,5-Diiodoaniline

Results obtained by practicing the above-mentioned standard operational process are set forth in the following table:

Table 42

| Example No. | N-(3,5-dihalo-phenyl)-succinic acid monoamide | Obtained N-(3,5-dihalophenyl)-imide compound | | | Elementary analysis | | | |
|---|---|---|---|---|---|---|---|---|
| | | Structural formula | Melting point | Yield (%) | C (%) | H (%) | N (%) | hal (%) |
| 29 | CH₃CHCOOH / CH₃CHCONH-phenyl-Cl,Cl | (imide structure with CH₃, Cl,Cl) | 110– 116° C | 96 | Calculated: 52.96  Found: 53.04 | 4.07  4.14 | 515  5.24 | (Cl) 26.06  26.03 |
| 30 | CH₃\CHCOOH / CH₃/CHCONH-phenyl-Br,Br | (imide structure with CH₃, Br,Br) | 125– 132° C | 93 | Calculated: 39.92  Found: 39.88 | 3.07  2.89 | 3.88  4.00 | (Br) 44.27  44.53 |

Table 42-continued

| Example No. | N-(3,5-dihalo-phenyl)-succinic acid monoamide | Obtained N-(3,5-dihalophenyl)-imide compound | | | | | | |
|---|---|---|---|---|---|---|---|---|
| | | Structural formula | Melting point | Yield (%) | Elementary analysis | | | |
| | | | | | C (%) | H (%) | N (%) | hal (%) |
| 31 | CH₃\CH(COOH)/CH(CH₃)/CONH—(3,5-diiodophenyl) | imide with 3,5-diiodophenyl | 137–140° C | 95 | Calculated: 31.67  Found: 31.28 | 2.44 2.71 | 3.08 3.23 | (I) 55.78 — |
| 32 | CH₃\CHCOOH / CHCONH—(3,5-dichlorophenyl), C₂H₅  Or  CH₃\CHCONH—(3,5-dichlorophenyl) / CH\COOH, C₂H₅ | imide with 3,5-dichlorophenyl, CH₃ and C₂H₅ substituents | 99–102° C | 92 | Calculated: 54.56  Found: 54.29 | 4.58 4.51 | 4.90 4.78 | (Cl) 24.78 24.85 |

EXAMPLES 33–37

Standard operational process:

A mixture comprising 0.1 mole of an N-(3',5'-dihalophenyl) succinic acid monoamide derivative, 50 ml. of acetic anhydride and 1 g. of anhydrous sodium acetate is fed to a 100 ml. four-necked flask and heated with stirring at 80° – 100° C. for 1 hour. Thereafter, the acetic acid and acetic anhydride are removed by distillation under reduced pressure, and the residue is washed with water and then dried, whereby a desired N-(3',5'-dihalophenyl) succinimide derivative represented by the formula (I) is obtained in a favorable yield. If necessary, recrystallization from ethanol is effected to obtain the desired product in a pure form.

The N-(3',5'-dihalophenyl) succinic acid monoamide employed in the above-mentioned process is easily synthesized according to an ordinary procedure from a corresponding succinic anhydride and an aniline.

Typical examples of the succinic anhydride and aniline are as set forth below, but it is needless to say that the scope of the present invention is not limited thereby.

Succinic anhydrides:

2-Fluorosuccinic anhydride
2-Chlorosuccinic anhydride
2-Bromosuccinic anhydride
2-Iodosuccinic anhydride
2,3-Difluorosuccinic anhydride
2,3-Dichlorosuccinic anhydride
2,3-Dibromosuccinic anhydride
2,3-Diiodosuccinic anhydride
Succinic anhydride Anilines:

3,5-Difluoroaniline
3,5-Dichloroaniline
3,5-Dibromoaniline
3,5-Diiodoaniline

Results obtained by practicing the above-mentioned standard operational process are set forth in the following table:

Table 43

| Example No. | N-(3',5'-dihalophenyl)-succinic acid monoamide | Obtained N-(3,5-dihalophenyl)-imide compound | | | | | | |
|---|---|---|---|---|---|---|---|---|
| | | Structural formula | Melting point | Yield (%) | Elementry analysis | | | |
| | | | | | C (%) | H (%) | N (%) | Cl (%) |
| 33 | Cl—CHCOOH / CH₂CONH—(3,5-dichlorophenyl)  Or  Cl—CHCONH—(3,5-dichlorophenyl) / CH₂COOH | imide with Cl and 3,5-dichlorophenyl | 128.5–129.5° C | 94 | Calculated: 43.12  Found: 42.98 | 2.17 2.04 | 5.03 5.17 | 38.19 37.97 |

Table 43-continued

Obtained N-(3,5-dihalopheny)-imide compound

| Example No. | N-(3',5'-dihalophenyl)-succinic acid monoamide | Structural formula | Melting point | Yield (%) | Elementry analysis Calculated/Found | C (%) | H (%) | N (%) | Cl (%) |
|---|---|---|---|---|---|---|---|---|---|
| 34 | Br—CHCOOH / CH₂CONH—(3,5-diCl-phenyl)  Or  Br—CHCONH—(3,5-diCl-phenyl) / CH₂COOH | 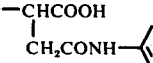 | 132 – 136° C | 93 | Calculated: Found: | 37.19 37.25 | 1.87 2.01 | 4.34 4.26 | |
| 35 | Cl—CHCOOH / Cl—CHCONH—(3,5-diCl-phenyl) | 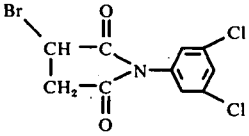 | 188 – 190° C | 90 | Calculated: found: | 38.38 38.31 | 1.61 1.50 | 4.48 4.32 | 45.31 45.57 |
| 36 | Cl—CHCOOH / CH₂CONH—(3,5-diBr-phenyl)  Or  Cl—CHCONH—(3,5-diBr-phenyl) / CH₂COOH | 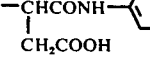 | 153.0 – 156.0° C | 90 | Calculated: Found: | 32.69 32.53 | 1.65 1.53 | 3.81 3.51 | |
| | Br—CHCOOH / Br—CHCONH—(3,5-diCl-phenyl) | 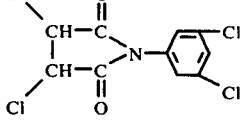 | 186 – 190° C | 91 | Calculated: Found: | 29.89 29.74 | 1.25 1.38 | 3.49 3.47 | |

EXAMPLES 38–47

Standard operational process:

A mixture comprising 0.1 mole of an N-phenylmaleimide, 0.1 mole of a thiol represented by the formula (IV) and 100 ml. of benzene is fed to a 200 ml. four-necked flask and charged under stirring with 5 ml. of benzene containing a catalytic amount of triethylamine, and the stirring is continued for additional 30 minutes. Thereafter, the benzene is removed by distillation under reduced pressure, whereby a desired N-phenylsuccinimide represented by the formula (I) is obtained in a favorable yield.

If necessary, recrystallization from benzeneligroin is effected to obtain the desired product in a pure form.

Typical examples of the N-phenylmaleimide and thiol employed in the above-mentioned process are as set forth below, but it is needless to say that the scope of the present invention is not limited thereby.

N-Phenylmaleimides:

N-(3,5-Difluorophenyl) maleimide
N-(3,5-Dichlorophenyl) maleimide
N-(3,5-Dibromophenyl) maleimide
N-(3,5-Diiodophenyl) maleimide Thiols:

Methyl mercaptan
Ethyl mercaptan
n-Propyl mercaptan
iso-Propyl mercaptan
n-Butyl mercaptan
iso-Butyl mercaptan
tert-Butyl mercaptan
n-Amyl mercaptan
iso-Amyl mercaptan
tert-Amyl mercaptan
act-Amyl mercaptan
Hexyl mercaptan
Heptyl mercaptan
Octyl mercaptan
Nonyl mercaptan
Decyl mercaptan
Thiophenol
o-Thiocresol
m-Thiocresol
p-Thiocresol
o-Chlorothiophenol
m-Chlorothiophenol
p-Chlorothiophenol
p-Nitrothiophenol
Benzyl mercaptan
Allyl mercaptan
Thioacetic acid Results obtained by practicing the above-mentioned standard operational process are set forth in the following table:

Table 44

| | | Obtained N-(3,5-dihalophenyl)-imide compound | | | | | | | |
|---|---|---|---|---|---|---|---|---|---|
| Example No. | Thiol derivative | Structural formula | Yield (%) | Physical constant (°C) | Elementary analysis (X: halogen atom) | | | | |
| | | | | | C(%) | H(%) | N(%) | S(%) | X(%) |
| 38 | $CH_3CH_2SH$ | [3,5-diCl-phenyl imide with -CH·SCH$_2$CH$_3$, -CH$_2$] | 85 | m.p. 104-106 | Calculated: 47.38 Found: 47.61 | 3.64 3.66 | 4.60 4.49 | 10.54 10.26 | (Cl) 23.31 23.16 |
| 39 | $CH_3(CH_2)_2CH_2SH$ | [3,5-diCl-phenyl imide with -CH·SCH$_2$(CH$_2$)$_2$·CH$_3$, -CH$_2$] | 83 | m.p. 60-61.5 | Calculated: 50.61 Found: 50.48 | 4.55 4.27 | 4.22 4.06 | 9.65 9.70 | (Cl) 21.34 21.39 |
| 40 | $CH_3(CH_2)_6CH_2SH$ | [3,5-diCl-phenyl imide with -CH-SCH$_2$(CH$_2$)$_6$·CH$_3$, -CH$_2$] | 86 | m.p. 47-51 | Calculated: 55.67 Found: 55.96 | 5.97 6.02 | 3.61 3.68 | 8.26 8.15 | (C) 18.26 18.12 |
| 41 | Ph-SH | [3,5-diCl-phenyl imide with -CH·S-Ph, -CH$_2$] | 95 | m.p. 150-151 | Calculated: 54.56 Found: 55.32 | 3.15 3.16 | 3.98 3.69 | 9.10 9.48 | (Cl) 20.13 20.43 |
| 42 | Cl-Ph-SH | [3,5-diCl-phenyl imide with -CH-S-Ph-Cl, -CH$_2$] | 90 | m.p. 119-120.5 | Calculated: 49.70 Found: 49.79 | 2.61 2.46 | 3.62 3.52 | 8.29 8.11 | (Cl) 27.51 27.30 |
| 43 | $CH_3$-Ph-SH | [3,5-diCl-phenyl imide with -CH-S-Ph-CH$_3$, -CH$_2$] | 90 | m.p. 145-147 | Calculated: 55.75 Found: 55.96 | 3.58 3.34 | 3.82 4.00 | 8.75 8.41 | (Cl) 19.36 19.00 |
| 44 | Ph-CH$_2$SH | [3,5-diCl-phenyl imide with -CH-SCH$_2$-Ph, -CH$_2$] | 85 | b.p. 0.1 mmHg 197-200 | Calculated: 55.74 Found: 55.71 | 3.58 3.35 | 3.82 3.62 | 8.75 8.57 | (Cl) 19.36 19.23 |
| 45 | Ph-SH | [3,5-diBr-phenyl imide with -CH-S-Ph, -CH$_2$] | 93 | m.p. 159.5-161 | Calculated: 43.56 Found: 43.31 | 2.51 2.58 | 3.18 3.00 | 7.27 7.40 | (Br) 36.23 36.51 |

Table 44-continued

| | | Obtained N-(3,5-dihalophenyl)-imide compound | | | | | | |
|---|---|---|---|---|---|---|---|---|
| Example No. | Thiol derivative | Structural formula | Yield (%) | Physical constant (°C) | Elementary analysis (X: halogen atom) | | | |
| | | | | | C(%) | H(%) | N(%) | S(%) X(%) |
| 46 | $CH_2=CH-CH_2SH$ | [structure: 3,5-dichlorophenyl succinimide with -CH-S-CH$_2$-CH=CH$_2$ substituent] | 93 | m.p. 81–82 | Calculated: 49.38 Found: 49.18 | 3.51 3.45 | 4.45 4.55 | 10.14 (Cl) 10.05 22.42 22.56 |
| 47 | $CH_3-\underset{\underset{O}{\|}}{C}-SH$ | [structure: 3,5-dichlorophenyl succinimide with -CH-S-C(=O)-CH$_3$ substituent] | 95 | m.p. 129.5–131.0 | Calculated: 45.30 Found: 45.48 | 2.86 2.77 | 4.40 4.29 | 10.08 (Cl) 10.15 22.28 22.30 |

EXAMPLES 48–52

Standard operational process:

A mixture comprising 0.1 mole of an N-phenylmaleimide, 0.1 mole of an amine represented by the formula (IV) and 100 ml. of benzene is fed to a 200 ml. four-necked flask and is stirred at a suitable temperature for 1 hour. Thereafter, the benzene is removed by distillation under reduced pressure, whereby a desired N-phenylsuccinimide represented by the formula (I) is obtained in a favorable yield.

If necessary, recrystallization from benzeneligroin is effected to obtain the desired product in a pure form.

Typical examples of the N-phenylmaleimide and amine employed in the above-mentioned process are as set forth below, but it is needless to say that the scope of the present invention is not limited thereby.

N-Phenylmaleimides:

N-(3,5-Difluorophenyl) maleimide
N-(3,5-Dichlorophenyl) maleimide
N-(3,5-Dibromophenyl) maleimide
N-(3,5-Diiodophenyl) maleimide Amines:

Dimethylamine
Diethylamine
Di-n-propylamine
Di-n-butylamine
Di-iso-butylamine
Di-n-amylamine
Di-iso-amylamine
Dihexylamine
Dicyclohexylamine
Diphenylamine
Pyrrolidine
Piperidine
Morpholine Results obtained by practicing the above-mentioned standard operational process are set forth in the following table:

Table 45

| | | Obtained N-(3,5-dihalophenyl)-imide compound | | | | | | |
|---|---|---|---|---|---|---|---|---|
| Example No. | Amine | Structural formula | Yield (%) | point (°C) | Elementary analysis | | | |
| | | | | | C(%) | H(%) | N(%) | Cl(%) |
| 48 | $CH_3CH_2$\ NH / $CH_3CH_2$ | [3,5-dichlorophenyl succinimide with -CH-N(CH$_2$CH$_3$)$_2$ substituent] | 83 | 95–96.5 | Calculated: 53.35 Found: 52.23 | 5.12 5.07 | 8.89 8.89 | 22.50 22.40 |
| 49 | $CH_3(CH_2)_2CH_2$\ NH / $CH_3(CH_2)_2CH_2$ | [3,5-dichlorophenyl succinimide with -CH-N(CH$_2$(CH$_2$)$_2$CH$_3$)$_2$ substituent] | 85 | 89–91 | Calculated: 58.22 Found: 58.22 | 6.52 6.70 | 7.54 7.36 | 19.10 19.29 |

Table 45-continued

| Example No. | Amine | Structural formula | Yield (%) | Melting point (°C) | Elementary analysis | | | |
|---|---|---|---|---|---|---|---|---|
| | | | | | C(%) | H(%) | N(%) | Cl(%) |
| 50 |  | 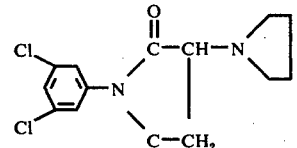 | 87 | 85–87 | Calculated: 53.69<br>Found: 53.58 | 4.51<br>4.45 | 8.95<br>8.74 | 22.64<br>22.81 |
| 51 |  | 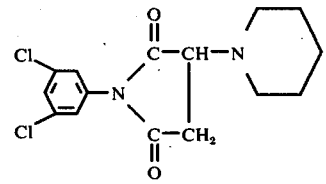 | 90 | 118–121 | Calculated: 55.06<br>Found: 55.22 | 4.93<br>4.85 | 8.56<br>8.44 | 21.67<br>21.80 |
| 52 | 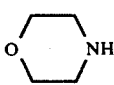 | 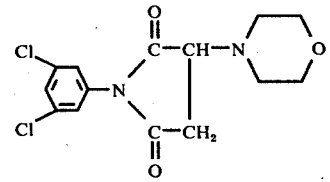 | 98 | 209–210 | Calculated: 51.08<br>Found: 50.88 | 4.29<br>4.45 | 8.51<br>8.31 | 21.54<br>21.21 |

EXAMPLES 53–55

Standard operational process:

Into a solution of 0.1 mole of an N-(3',5'-dihalophenyl) maleimide derivative in 100 ml. of tetrahydrofuran is introduced dry hydrogen chloride gas at 25° C. for 1 hour, and then stirring is effected for 3 hours. After completion of the reaction, the solvent is removed by distillation under reduced pressure, whereby a desired N-(3,5-dihalophenyl) succinimide derivative represented by the formula (I) is obtained in a favorable yield. If necessary, recrystallization from benzene-ethanol is effected to obtain the desired product in a pure form.

Examples of the N-(3',5'-dihalophenyl) maleimide derivative employed in the above-mentioned process are as follows:

N-(3',5'-Difluorophenyl) maleimide
N-(3',5'-Dichlorophenyl) maleimide
N-(3',5'-Dibromophenyl) maleimide
N-(3',5'-Diiodophenyl) maleimide Results obtained by practicing the above-mentioned standard operational process are shown in the following table:

Table 46

| Example No. | N-(3',5'-dihalophenyl)-maleimide | Hydrogen halide | Structural formula | Melting point | Yield (%) | Elementary analysis | | | |
|---|---|---|---|---|---|---|---|---|---|
| | | | | | | C(%) | H(%) | N(%) | Cl(%) |
| 53 | 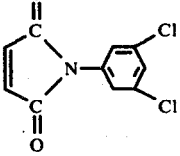 | Hydrogen chloride | 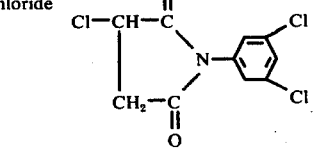 | 128.0–129.0° C | 93 | Calculated: 43.12<br>Found: 43.22 | 2.17<br>1.93 | 5.03<br>4.99 | 38.19<br>38.17 |
| 54 | 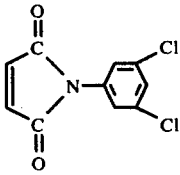 | Hydrogen bromide | 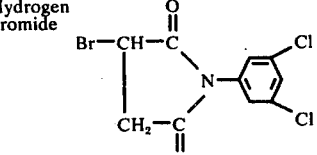 | 131–134° C | 86 | Calculated: 37.19<br>Found: 37.28 | 1.87<br>1.66 | 4.34<br>4.49 | |

Table 46-continued

| Ex-ample No. | N-(3',5'-dihalophenyl)-maleimide | Hydrogen halide | Obtained N-(3,5-dihalophenyl)-imide compound | | | | | | |
|---|---|---|---|---|---|---|---|---|---|
| | | | Structural formula | Melting point | Yield (%) | Elementary analysis | | | |
| | | | | | | | C(%) | H(%) | N(%) | Cl(%) |
| 55 | 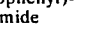 | Hydrogen chloride | 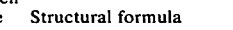 | 157–159.5° C | 91 | Calculated: 32.69<br>Found: 32.58 | 1.65<br>1.73 | 3.81<br>3.74 | |

EXAMPLES 56–57

Standard operational process:

0.1 Mole of an N-(3',5'-dihalophenyl) maleamic acid derivative is fed to a 100 ml. four-necked flask. Into this derivative is gradually dropped with stirring 50 g. of thionyl chloride, and then the stirring is continued under reflux for 1 hour. After completion of the reaction, the reaction liquid is charged into ice water to decompose excess thionyl chloride. In this case, crystals deposited are recovered by filtration and are dried after thorough washing with water, whereby an N-(3',5'-dihalophenyl)-3-chlorosuccinimide derivative represented by the formula (I) is obtained in a favorable yield. Recrystallization from benzene-ethanol gives the desired product in a pure form.

Examples of the N-(3',5'-dihalophenyl) maleamic acid derivative employed in the above-mentioned process are as follows:

N-(3',5'-Difluorophenyl) maleamic acid
N-(3',5'-Dichlorophenyl) maleamic acid
N-(3',5'-Dibromophenyl) maleamic acid
N-(3',5'-Diiodophenyl) maleamic acid Results obtained by practicing the above-mentioned standard operational process are shown in the following table:

A mixture comprising 0.1 mole of an N-phenylsuccinimide derivative and 100 ml. of acetone is fed to a 300 ml. four-necked flask. The mixture is charged with 0.3 mole of a 10% aqueous hydrogen peroxide solution and then stirred at 50° C. for 5 hours.

Subsequently, the reaction mixture is poured into ice water, and crystals deposited are filtered, water-washed and dried, whereby a desired N-phenylsuccinimide derivative represented by the formula (I) is obtained in a favorable yield.

The N-phenylsuccinimide derivative employed in the above-mentioned process is easily synthesized according to an ordinary procedure from an N-(3,5-dihalophenyl) maleimide and a thiol.

Typical examples of the N-(3,5-dihalophenyl) maleimide and thiol are as set forth below, but it is needless to say that the scope of the present invention is not limited thereby.

N-(3,5-Dihalophenyl) maleimides:

N-(3,5-Difluorophenyl) maleimide
N-(3,5-Dichlorophenyl) maleimide
N-(3,5-Dibromophenyl) maleimide
N-(3,5-Diiodophenyl) maleimide Thiols:

Methyl mercaptan

Table 47

| Ex-ample No. | N-(3',5'-dihalophenyl)-maleic acid monoamide | Dehydrating agent | Obtained N-(3,5-dihalophenyl)-imide compound | | | | | | |
|---|---|---|---|---|---|---|---|---|---|
| | | | Structural formula | Melting point | Yield (%) | Elementary analysis | | | |
| | | | | | | | C(%) | H(%) | N(%) | Cl(%) |
| 56 |  | Phosphorus pentachloride | 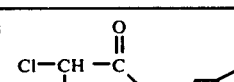 | 127.0–129.0° C | 87 | Calculated: 43.12<br>Found: 43.33 | 2.17<br>2.07 | 5.03<br>4.89 | 38.19<br>38.25 |
| 57 |  | Thionyl chloride | 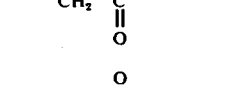 | 152.5–155.5° C | 84 | Calculated: 32.69<br>Found: 32.78 | 1.65<br>1.46 | 3.81<br>3.74 | |

EXAMPLES 58–61

Standard operational process:

Ethyl mercaptan
n-Propyl mercaptan
iso-Propyl mercaptan
n-Butyl mercaptan iso-Butyl mercaptan
tert-Butyl mercaptan
n-Amyl mercaptan
iso-Amyl mercaptan
tert-Amyl mercaptan
act-Amyl mercaptan
Hexyl mercaptan
Heptyl mercaptan
Octyl mercaptan
Nonyl mercaptan
Decyl mercaptan
Benzyl mercaptan Results obtained by practicing the above-mentioned standard operational process are shown in the following table:

EXAMPLE 63

Dust:

4 Parts of 1-(3′,5′-dichlorophenyl)-3-ethylthio-2,5-pyrrolidine-dione and 96 parts of talc were thoroughly pulverized and mixed together to obtain a dust containing 4% of active ingredient. In application, the dust was dusted as it was.

EXAMPLE 64

Wettable powder:

50 Parts of 1-(3′,5′-dichlorophenyl)-3-(p-chlorophenylthio)-2,5-pyrrolidine-dione, 5 parts of a wetting agent (alkylbenzenesulfonate type) and 45 parts of diatomaceous earth were thoroughly pulverized and mixed together to obtain a wettable powder containing Table 48

| Example No. | N-Phenyl succinimide derivative | Obtained N-(3,5-dihalophenyl)-imide compound | | | | | | |
|---|---|---|---|---|---|---|---|---|
| | | Structural formula | Melting point | Yield (%) | Elementary analysis | | | |
| | | | | | C(%) | H(%) | N(%) | Cl(%) | S(%) |
| 58 | [structure: 3,5-dichlorophenyl succinimide with CH–SCH₂CH₃] | [structure: with CH–SO, CH₂CH₃] | 150–151° C | 95 | Calculated: 45.01 Found: 45.15 | 3.47 3.25 | 4.38 4.45 | 22.1 22.03 | 10.01 10.22 |
| 59 | [structure with CH–S, CH₂(CH₂)₂CH₃] | [structure with CH–SO, CH₂(CH₂)₂CH₃] | 143–144° C | 93 | Calculated: 48.28 Found: 48.40 | 4.34 4.31 | 4.02 3.75 | 20.36 20.09 | 9.21 9.39 |
| 60 | [structure with CH–S, CH₂(CH₂)₆CH₃] | [structure with CH–SO, CH₂(CH₂)₆CH₃] | 122–124° C | 92 | Calculated: 53.33 Found: 53.10 | 5.98 5.82 | 3.46 3.62 | 17.49 17.33 | 7.91 8.07 |
| 61 | [structure with CH–S, CH₂–phenyl] | [structure with CH–SO, CH₂–phenyl] | 162–163.5° C | 96 | Calculated: 53.41 Found: 53.41 | 3.43 3.43 | 3.66 3.54 | 18.55 18.35 | 8.39 8.59 |

Examples 21–10 are concerned with the formulation of microbicidal compositions containing the present compounds.

EXAMPLE 62

Dust:

3 Parts of 1-(3′,5′-dichlorophenyl)-3-phenylthio-2,5-pyridine-dione and 97 parts of clay were thoroughly pulverized and mixed together to obtain a dust containing 3% of active ingredient. In application, the dust was dusted as it was.

50% of active ingredient. In application, the wettable powder was diluted with water, and the solution was sprayed.

EXAMPLE 65

Emulsifiable concentrate:

10 Parts of 1-(3′,5′-dichlorophenyl)-3-diethylamino-2,5-pyrrolidine-dione, 80 parts of dimethyl sulfoxide and 10 parts of an emulsifier (polyoxyethylene phenylphenol ether type) were mixed together to obtain an emulsifiable concentrate containing 10% of active ingredient. In application, the concentrate was diluted with water, and the resulting emulsion was sprayed.

EXAMPLE 66

Granule:

5 Parts of 1-(3',5'-dichlorophenyl)-3-n-butylthio-2,5-pyrrolidine-dione, 93.5 parts of clay and 1.5 parts of a binding agent (polyvinyl alcohol type) were thoroughly pulverized and mixed together. After kneading with water, the mixture was granulated and dried to obtain a granule containing 5% of active ingredient. Granule was applied as it was.

EXAMPLE 67

Mixed dust:

2 Parts of 1-(3',5'-dichlorophenyl)-3-pyrrolidino-2,5-pyrrolidine-dione, 1.5 parts of O-n-butyl-S-ethyl-S-benzylphosphorodithiolate, 0.1 part of Kasugamycin and 96.4 parts of clay were thoroughly pulverized and mixed together to obtain a dust containing 3.6% of active ingredient. In application, the dust was dusted as it was.

EXAMPLE 68

Mixed dust:

2 Parts of 1-(3',5'-dichlorophenyl)-3-p-tolylthio-2,5-pyrrolidine-dione, 1.5 parts of O-n-butyl-S-ethyl-S-benzylphosphorodithiolate, 2 parts of OO-dimethyl-O-(3-methyl-4-nitrophenyl) phosphorothioate, 1.5 parts of 3,4-dimethylphenyl-N-methylcarbamate and 93 parts of clay were thoroughly pulverized and mixed together to obtain a dust containing 7% of active ingredient. In application, the dust was dusted as it was.

EXAMPLE 69

Dust:

3 Parts of N-(3',5'-dichlorophenyl) cyclopropanedicarboximide and 97 parts of clay were thoroughly pulverized and mixed together to obtain a dust containing 3% of active ingredient. In application, the dust was dusted as it was.

EXAMPLE 70

Dust:

4 Parts of N-(3',5'-dibromophenyl) cyclopropanedicarboximide and 96 parts of talc were thoroughly pulverized and mixed together to obtain a dust containing 4% of active ingredient. In application, the dust was dusted as it was.

EXAMPLE 71

Wettable powder:

50 Parts of 1,2-dimethyl-N-(3',5'-dichlorophenyl) cyclopropanedicarboximide, 5 parts of a wetting agent (alkylbenzenesulfonate type) and 45 parts of diatomaceous earth were thoroughly pulverized and mixed together to obtain a wettable powder containing 50% of active ingredient. In application, the wettable powder was diluted with water, and the solution was sprayed.

EXAMPLE 72

Emulsifiable concentrate:

10 Parts of 1,3-dimethyl-N-(3',5'-dichlorophenyl) cyclopropanedicarboximide, 80 parts of dimethyl sulfoxide and 10 parts of an emulsifier (polyoxyethylene phenylphenol ether type) were mixed together to obtain an emulsifiable concentrate containing 10% of active ingredient. In application, the concentrate was diluted with water, and the resulting emulsion was sprayed.

EXAMPLE 73

Granule:

5 Parts of 1,3-dimethyl-N-(3',5'-dibromophenyl) cyclopropanedicarboximide, 93.5 parts of clay and 1.5 parts of a binding agent (polyvinyl alcohol type) were thoroughly pulverized and mixed together, and the mixture was kneaded with water and then granulated and dried to obtain a granule containing 5% of active ingredient. Granule was applied as it was.

EXAMPLE 74

Mixed dust:

3.6 Parts of 1,3-dimethyl-N-(3',5'-diiodophenyl) cyclopropanedicarboximide, 1.5 parts of O-n-butyl-S-ethyl-S-benzyl-phosphorodithiolate, 0.1 part of Kasugamycin and 96.4 parts of clay were thoroughly pulverized and mixed together to obtain a mixed dust containing 3.6% of active ingredient. In application, the dust was dusted as it was.

EXAMPLE 75

Mixed dust:

7 Parts of N-(3',5'-dichlorophenyl) cyclopropanedicarboximide, 1.5 parts of O-n-butyl-S-ethyl-S-benzyl phosphorodithiolate, 2 parts of O,O-dimethyl-O-(3-methyl-4-nitrophenyl) phosphorothioate, 1.5 parts of 3,4-dimethylphenyl-N-methylcarbamate and 93 parts of clay were thoroughly pulverized and mixed together to obtain a mixed dust containing 7% of active ingredient. In application, the dust was dusted as it was.

EXAMPLE 76

Dust:

3 parts of N-(3,5-dichlorophenyl) glutarimide and 97 parts of clay were thoroughly pulverized and mixed together to obtain a dust containing 3% of active ingredient. In application, the dust was dusted as it was.

EXAMPLE 77

Dust:

4 Parts of N-(3,5-dibromophenyl) glutarimide and 96 parts of talc were thoroughly pulverized and mixed together to obtain a dust containing 4% of active ingredient. In application, the dust was dusted as it was.

EXAMPLE 78.

Wettable powder:

50 Parts of N-(3,5-diiodophenyl) glutarimide, 5 parts of a wetting agent (alkylbenzenesulfonate type) and 45 parts of diatomaceous earth were thoroughly pulverized and mixed together to obtain a wettable powder containing 50% of active ingredient. In application, the wettable powder was diluted with water, and the solution was sprayed.

EXAMPLE 79

Emulsifiable concentrate:

10 Parts of N-(3,5-dichlorophenyl) glutarimide, 80 parts of dimethyl sulfoxide and 10 parts of an emulsifier (polyoxyethylene phenylphenol type) were mixed together to obtain an emulsifiable concentrate containing 10% of active ingredient. In application, the concentrate was diluted with water, and the resulting emulsion was sprayed.

EXAMPLE 80

Granule:

5 Parts of N-(3,5-dibromophenyl) glutarimide, 93.5 parts of clay and 1.5 parts of a binding agent (polyvinyl alcohol type) were thoroughly pulverized and mixed together, and the mixture was kneaded with water and then granulated and dried to obtain a granule containing 5% of active ingredient. Granule was applied as it was.

EXAMPLE 81

Mixed dust:

2 parts of N-(3,5-dichlorophenyl) glutarimide, 1.5 parts of O-n-butyl-S-ethyl-S-benzyl phosphorodithiolate, 0.1 part of Kasugamycin and 96.4 parts of clay were thoroughly pulverized and mixed together to obtain a dust containing 3.6% of active ingredient.

EXAMPLE 82

Mixed dust:

2 Parts of N-(3,5-dichlorophenyl) glutarimide, 1.5 parts of O-n-butyl-S-ethyl-S-benzyl phosphorodithiolate, 2 parts of O,O-dimethyl-O-(3-methyl-4-nitrophenyl) phosphorothioate, 1.5 parts of 3,4-dimethylphenyl-N-methylcarbamate were thoroughly pulverized and mixed together to obtain a dust containing 7% of active ingredient. In application, the dust was dusted as it was.

EXAMPLE 83

Dust:

3 Parts of N-(3,5-dichlorophenyl)-imide of $\Delta'$-cyclohexenedicarboxylic acid and 97 parts of clay were thoroughly pulverized and mixed together to obtain a dust containing 3% of active ingredient. In application, the dust was dusted as it was.

EXAMPLE 84

Dust:

4 Parts of N-(3,5-dichlorophenyl)-imide of $\Delta'$-cyclohexenedicarboxylic acid and 96 parts of talc were thoroughly pulverized and mixed together to obtain a dust containing 4% of active ingredient. In application, the dust was dusted as it was.

EXAMPLE 85

Wettable powder:

50 Parts of N-(3,5-dichlorophenyl)-imide of $\Delta^{1,4}$-cyclohexadienedicarboxylic acid, 5 parts of a wetting agent (alkylbenzenesulfonate type) and 45 parts of diatomaceous earth were thoroughly pulverized and mixed together to obtain a wettable powder containing 50% of active ingredient. In application, the wettable powder was diluted with water, and the solution was sprayed.

EXAMPLE 86

Emulsifiable concentrate:

10 Parts of N-(3,5-dichlorophenyl) phthalimide, 80 parts of dimethyl sulfoxide and 10 parts of an emulsifier (polyoxyethylene phenylphenol ether type) were mixed together to obtain an emulsifiable concentrate containing 10% of active ingredient. The wettable powder was diluted with water, and the solution was applied.

EXAMPLE 87

Granule:

5 Parts of N-(3,5-dichlorophenyl)-imide of cyclohexane-1,2-dicarboxylic acid, 93.5 parts of clay and 1.5 parts of a binding agent (polyvinyl alcohol type) were thoroughly pulverized and mixed together, and the mixture was kneaded with water and then granulated and dried to obtain a granule containing 5% of active ingredient. Granule was applied as it was.

EXAMPLE 88

Mixed dust:

2 Parts of N-(3,5-dichlorophenyl)-imide of $\Delta'$-cyclohexenedicarboxylic acid, 1.5 parts of O-n-butyl-S-ethyl-S-benzyl phosphorodithiolate, 0.1 part of Kasugamycin and 96.4 parts of clay were thoroughly pulverized and mixed together to obtain a dust containing 3.6% of active ingredient. In application, the dust was dusted as it was.

EXAMPLE 89

Mixed dust:

2 Parts of N-(3,5-dibromophenyl)-imide of $\Delta'$-cyclohexenedicarboxylic acid, 1.5 parts of O-n-butyl-S-ethyl-S-benzyl phosphorodithiolate, 2 parts of O,O-dimethyl-O-(3-methyl-4-nitrophenyl) phosphorothioate, 1.5 parts of 3,4-dimethylphenyl-N-methylcarbamate and 93 parts of clay were thoroughly pulverized and mixed together to obtain a dust containing 7% of active ingredient. In application, the dust was dusted as it was.

EXAMPLE 90

Dust:

3 Parts of N-(3,5-dichlorophenyl)-$\alpha,\beta$-dimethylsuccinimide and 97 parts of clay were thoroughly pulverized and mixed together to obtain a dust containing 3% of active ingredient.

EXAMPLE 91

Dust:

4 Parts of N-(3,5-dibromophenyl)-$\alpha,\beta$-dimethylsuccinimide and 96 parts of talc were thoroughly pulverized and mixed together to obtain a dust containing 4% of active ingredient. In application, the dust was dusted as it was.

EXAMPLE 92

Wettable powder:

50 Parts of N-(3,5-diiodophenyl)-$\alpha,\beta$-dimethylsuccinimide, 5 parts of a wetting agent (alkylbenzenesulfonate type) and 45 parts of diatomaceous earth were thoroughly pulverized and mixed together to obtain a wettable powder containing 50% of active ingredient. In application, the wettable powder was diluted with water, and the solution was sprayed.

EXAMPLE 93

Emulsifiable concentrate:

10 Parts of N-(3,5-dichlorophenyl)-$\alpha,\beta$-dimethylsuccinimide, 80 parts of dimethyl sulfoxide and 10 parts of an emulsifier (polyoxyethylene phenylphenol ether type) were mixed together to obtain an emulsifiable concentrate containing 10% of active ingredient. In application, the concentrate was diluted with water, and the resulting emulsion was sprayed.

EXAMPLE 94

Granule:

5 Parts of N-(3,5-dichlorophenyl)-α,β-dimethylsuccinimide, 93.5 parts of clay and 1.5 parts of a binding agent (polyvinyl alcohol type) were thoroughly pulverized and mixed together, and the mixture was kneaded with water and then granulated and dried to obtain a granule containing 5% of active ingredient. Granule was applied as it was.

EXAMPLE 95

Mixed dust:

2 Parts of N-(3,5-dichlorophenyl)-α,β-dimethylsuccinimide, 1.5 parts of O-n-butyl-S-ethyl-S-benzyl phosphorodithiolate, 0.1 part of Kasugamycin and 96.4 parts of clay were thoroughly pulverized and mixed together to obtain a dust containing 3.6% of active ingredient. In application, the dust was dusted as it was.

EXAMPLE 96

Mixed dust:

2 Parts of N-(3,5-dibromophenyl)-α,β-dimethylsuccinimide, 1.5 parts of O-n-butyl-S-ethyl-S-benzyl phosphorodithiolate, 2 parts of O,O-dimethyl-O-(3-methyl-4-nitrophenyl) phosphorothioate, 1.5 parts of 3,4-dimethylphenyl-N-methylcarbamate and 93 parts of clay were thoroughly pulverized and mixed together to obtain a dust containing 7% of active ingredient. In application, the dust was dusted as it was.

EXAMPLE 97

Dust:

3 Parts of N-(3,5-dichlorophenyl)-chlorosuccinimide and 97 parts of clay were thoroughly pulverized and mixed together to obtain a dust containing 3% of active ingredient. In application, the dust was dusted as it was.

EXAMPLE 98

Dust:

4 Parts of N-(3,5-dibromophenyl)-bromosuccinimide and 96 parts of talc were thoroughly pulverized and mixed together to obtain a dust containing 4% of active ingredient. In application, the dust was dusted as it was.

EXAMPLE 99

Wettable powder:

50 Parts of N-(3,5-dichlorophenyl)-α,β-dichlorosuccinimide, 5 parts of a wetting agent (alkylbenzenesulfonate type) and 45 parts of diatomaceous earth were thoroughly pulverized and mixed together to obtain a wettable powder containing 50% of active ingredient. In application, the wettable powder was diluted with water, and the solution was sprayed.

EXAMPLE 100

Emulsifiable concentrate:

10 Parts of N-(3,5-dibromophenyl)-chlorosuccinimide, 80 parts of dimethyl sulfoxide and 10 parts of an emulsifier (polyoxyethylene phenylphenol ether type) were mixed together to obtain an emulsifiable concentrate containing 10% of active ingredient. In application, the concentrate was diluted with water, and the resulting emulsion was sprayed.

EXAMPLE 101

Granule:

5 Parts of N-(3,5-dichlorophenyl)-α,β-dibromosuccinimide, 93.5 parts of clay and 1.5 parts of a binding agent (polyvinyl alcohol type) were thoroughly pulverized and mixed together, and the mixture was kneaded with water and then granulated and dried to obtain a granule containing 5% of active ingredient. Granule was applied as it was.

EXAMPLE 102

Mixed dust:

2 Parts of N-(3,5-dichlorophenyl)-chlorosuccinimide, 1.5 parts of O-n-butyl-S-ethyl-S-benzyl phosphorodithiolate, 0.1 part of Kasugamycin and 96.4 parts of clay were thoroughly pulverized and mixed together to obtain a dust containing 3.6% of active ingredient. In application, the dust was dusted as it was.

EXAMPLE 103

Mixed dust:

2 Parts of N-(3,5-dichlorophenyl)-α,β-dichlorosuccinimide, 1.5 parts of O-n-butyl-S-ethyl-S-benzyl phosphorodithiolate, 2 parts of O,O-dimethyl-O-(3-methyl-4-nitrophenyl) phosphorothioate, 1.5 parts of 3,4-dimethylphenyl-N-methylcarbamate and 93 parts of clay were thoroughly pulverized and mixed together to obtain a dust containing 7% of active ingredient. In application, the dust was dusted as it was.

EXAMPLE 104

Dust:

3 Parts of N-(3,5-dichlorophenyl)-ethylsulfinylsuccinimide and 97 parts of clay were thoroughly pulverized and mixed together to obtain a dust containing 3% of active ingredient. In application, the dust was dusted as it was.

EXAMPLE 105

Dust:

4 Parts of N-(3,5-dichlorophenyl)-n-octylsulfinylsuccinimide and 96 parts of talc were thoroughly pulverized and mixed together to obtain a dust containing 4% of active ingredient. In application, the dust was dusted as it was.

EXAMPLE 106

Wettable powder:

50 Parts of N-(3,5-dichlorophenyl)-benzylsulfinylsuccinimide, 5 parts of a wetting agent (alkylbenzenesulfonate type) and 45 parts of diatomaceous earth were thoroughly pulverized and mixed together to obtain a wettable powder containing 50% of active ingredient. In application, the wettable powder was diluted with water, and the solution was sprayed.

EXAMPLE 107

Emulsifiable concentrate:

10 Parts of N-(3,5-dichlorophenyl)-n-octylsulfinylsuccinimide, 80 parts of dimethyl sulfoxide and 10 parts of an emulsifier (polyoxyethylene phenylphenol ether type) were mixed together to obtain an emulsifiable concentrate containing 10% of active ingredient. In application, the concentrate was diluted with water, and the resulting emulsion was sprayed.

EXAMPLE 108

Granule:

5 Parts of N-(3,5-dichlorophenyl)-n-octylsulfinylsuccinimide, 93.5 parts of clay and 1.5 parts of a binding agent (polyvinyl alcohol type) were thoroughly pulverized and mixed together, and the mixture was kneaded with water and then granulated and dried to obtain a granule containing 5% of active ingredient. Granule was applied as it was.

EXAMPLE 109

Mixed dust:

2 Parts of N-(3,5-dichlorophenyl)-benzylsulfinylsuccinimide, 1.5 parts of O-n-butyl-S-ethyl-S-benzyl phosphorodithiolate, 0.1 part of Kasugamycin and 96.4 parts of clay were thoroughly pulverized and mixed together to obtain a dust containing 3.6% of active ingredient. In application, the dust was dusted as it was.

EXAMPLE 110

Mixed dust:

2 Parts of N-(3,5-dichlorophenyl)-ethylsulfinylsuccinimide, 1.5 parts of O-n-butyl-S-ethyl-S-benzyl phosphorodithiolate, 2 parts of O,O-dimethyl-O-(3-methyl-4-nitrophenyl) phosphorothioate, 1.5 parts of 3,4-dimethylphenyl-N-methylcarbamate and 93 parts of clay were thoroughly pulverized and mixed together to obtain a dust containing 7% of active ingredient. In application, the dust was dusted as it was.

What we claim is:

1. A microbiocidal composition containing as an active ingredient an anti-microbiocidally effective amount of an N-(3,5-dihalophenyl)imide compound represented by the formula,

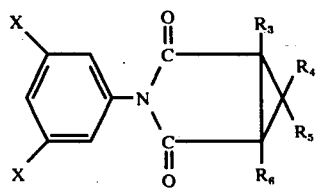

wherein X represents, Cl, Br or I; $R_3$, $R_4$ and $R_6$ each represent hydrogen or methyl; and $R_5$ represents hydrogen or methyl and a carrier.

2. A microbiocidal composition according to claim 1 wherein said N-(3,5-dihalophenyl)imide compound is represented by the formula,

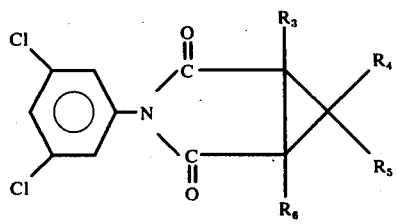

wherein $R_3$, $R_4$, $R_5$ and $R_6$ are the same as defined in claim 1.

3. A microbiocidal composition according to claim 1 wherein said N-(3,5-dihalophenyl)imide compound is represented by the formula,

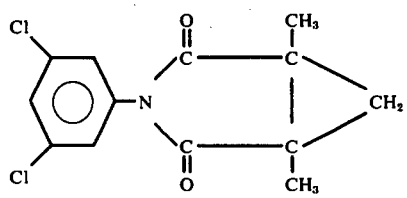

4. A microbiocidal composition according to claim 1 wherein said N-(3,5-dihalophenyl)imide compound is represented by the formula,

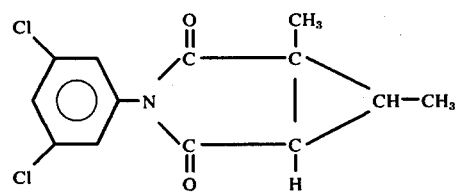

5. A microbiocidal composition according to claim 1 wherein the composition is a dust, wettable powder, emulsifiable concentrate, granule, aerosol, oil spray, tablet, pellet, ointment or powder.

6. A method for controlling microorganisms, which comprises contacting the microorganisms with an anti-microbiocidally effective amount of an N-(3,5-dihalophenyl)imide compound represented by the formula,

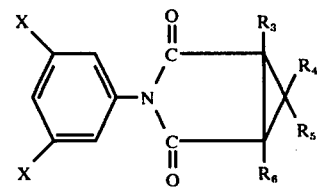

wherein X represents Cl, Br or I; $R_3$, $R_4$ and $R_6$ each represents hydrogen or methyl; and $R_5$ represents hydrogen or methyl.

7. A method for controlling microorganisms as claimed in claim 6, wherein said N-(3,5-dihalophenyl)imide compound is represented by the formula,

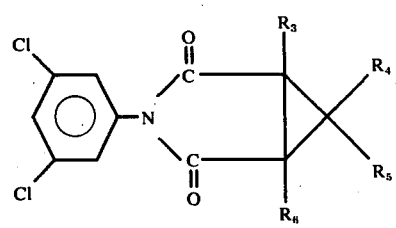

wherein $R_3$, $R_4$, $R_5$ and $R_6$ are the same as defined in claim 6.

8. A method for controlling microorganisms according to claim 6, wherein said N-(3,5-dihalophenyl)imide compound is of the formula,

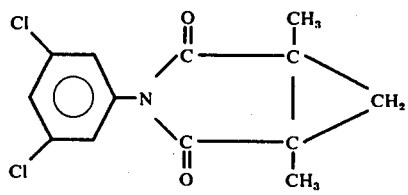
9. A method for controlling microorganisms according to claim 6, wherein said N-(3,5-dihalophenyl)imide compound is of the formula,
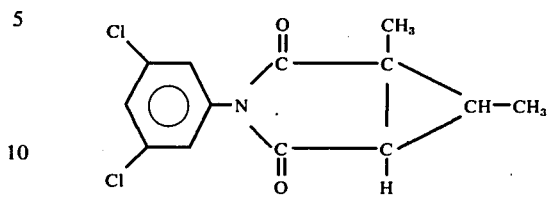
* * * * *